United States Patent
Garimella

(10) Patent No.: US 7,687,437 B2
(45) Date of Patent: *Mar. 30, 2010

(54) METHOD FOR IMMOBILIZING MOLECULES ONTO SURFACES

(75) Inventor: Viswanadham Garimella, Evanston, IL (US)

(73) Assignee: Nanosphere, Inc., Northbrook, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/194,138

(22) Filed: Jul. 12, 2002

(65) Prior Publication Data
US 2003/0082588 A1    May 1, 2003

Related U.S. Application Data

(60) Provisional application No. 60/305,369, filed on Jul. 13, 2001, provisional application No. 60/363,472, filed on Mar. 12, 2002.

(51) Int. Cl.
*C40B 50/18*    (2006.01)
*G01N 33/552*    (2006.01)

(52) U.S. Cl. ......................................... 506/32; 436/527

(58) Field of Classification Search ................. 436/518, 436/524, 527, 106, 109, 127; 435/4, 6, 174; 506/32
See application file for complete search history.

(56) References Cited

U.S. PATENT DOCUMENTS

| | | | |
|---|---|---|---|
| 4,059,685 A | 11/1977 | Johnson | 424/12 |
| 4,067,959 A | 1/1978 | Bolz | 424/1 |
| 4,275,149 A | 6/1981 | Litman et al. | 435/7 |
| 4,751,177 A | 6/1988 | Stabinsky | 435/6 |
| 4,797,355 A | 1/1989 | Stabinsky | 435/6 |
| 4,824,776 A | 4/1989 | Heller | 435/6 |
| 4,847,159 A | 7/1989 | Glajch et al. | 428/447 |
| 4,853,335 A | 8/1989 | Olsen et al. | 436/527 |
| 4,877,745 A | 10/1989 | Hayes et al. | 436/166 |
| 4,886,741 A | 12/1989 | Schwartz | 435/5 |
| 5,057,301 A | 10/1991 | Wilbur et al. | 530/363 |
| 5,071,978 A | 12/1991 | San | 536/124 |
| 5,109,124 A | 4/1992 | Ramachandran et al. | 536/27 |
| 5,114,674 A | 5/1992 | Stanbro et al. | 422/57 |
| 5,124,246 A | 6/1992 | Urdea et al. | 435/6 |
| 5,143,854 A | 9/1992 | Pirrung et al. | 436/518 |
| 5,233,369 A | 8/1993 | Carlotta et al. | 346/140 |
| 5,314,731 A | 5/1994 | Yoneda et al. | 428/429 |
| 5,324,633 A | 6/1994 | Fodor et al. | 436/5 |
| 5,342,867 A | 8/1994 | Ryan et al. | 524/101 |
| 5,399,501 A | 3/1995 | Pope et al. | |
| 5,482,867 A | 1/1996 | Barrett et al. | 436/518 |
| 5,486,855 A | 1/1996 | Carlotta et al. | 347/87 |
| 5,514,785 A | 5/1996 | Van Ness et al. | 536/22.1 |
| 5,527,673 A | 6/1996 | Reinhartz et al. | 435/6 |
| 5,532,170 A | 7/1996 | Buckle et al. | |
| 5,567,294 A | 10/1996 | Dovichi et al. | |
| 5,567,295 A | 10/1996 | Swamy et al. | 205/125 |
| 5,585,275 A | 12/1996 | Hudson et al. | 436/518 |
| 5,591,646 A | 1/1997 | Hudson et al. | 436/518 |
| 5,599,695 A | 2/1997 | Pease et al. | 435/91.1 |
| 5,622,826 A | 4/1997 | Varma | 435/6 |
| 5,624,711 A | 4/1997 | Sundberg et al. | 427/261 |
| 5,631,734 A | 5/1997 | Stern et al. | 356/317 |
| 5,690,894 A | 11/1997 | Pinkel et al. | 422/68.1 |
| 5,717,083 A * | 2/1998 | Cook et al. | 536/23.1 |
| 5,770,456 A | 6/1998 | Holmes | 436/518 |
| 5,773,308 A | 6/1998 | Conrad et al. | 436/527 |
| 5,831,070 A | 11/1998 | Pease et al. | 536/25.3 |
| 5,837,196 A | 11/1998 | Pinkel et al. | 422/55 |
| 5,837,454 A * | 11/1998 | Cozzette et al. | 435/6 |
| 5,840,190 A | 11/1998 | Scholander et al. | 210/500.24 |
| 5,858,653 A | 1/1999 | Duran et al. | 435/6 |
| 5,868,936 A | 2/1999 | Ofsthun et al. | 210/649 |
| 5,871,649 A | 2/1999 | Ofsthun et al. | 210/645 |
| 5,919,523 A * | 7/1999 | Sundberg et al. | 427/333 |
| 5,959,098 A | 9/1999 | Goldberg et al. | 536/25.3 |
| 6,004,752 A | 12/1999 | Loewy et al. | 435/6 |
| 6,004,755 A | 12/1999 | Wang | 435/6 |
| 6,013,440 A | 1/2000 | Lipshutz et al. | 435/6 |
| 6,040,138 A | 3/2000 | Lockhart et al. | 435/6 |

(Continued)

FOREIGN PATENT DOCUMENTS

EP    0 245 206 A1    11/1987

(Continued)

OTHER PUBLICATIONS

Guo et al., "Direct fluorescence analysis of genetic polymorphisms by hybridization with oligonucleotide arrays on glass supports", 1994, Nucleic Acids Research, 22(24), pp. 5456-5465.*

(Continued)

*Primary Examiner*—Amber D. Steele
(74) *Attorney, Agent, or Firm*—Gregory T. Pletta

(57) ABSTRACT

A method for immobilizing amino-group containing molecules onto surfaces and devices having immobilized isocyanate-group containing molecules prepared by the method are disclosed. The method comprises reacting a surface (i.e., glass surface) having free hydroxyl groups with a silyl isocyanate derivatizing agent to provide immobilized reactive moieties, the agent having a formula:

$$(R_1O)(R_2O)(R_3O)Si-X-NCO$$

wherein $R_1$, $R_2$ and $R_3$ are independently represents $C_1$-$C_6$ alkyl, phenyl, or aryl substituted with one or more groups selected from the group consisting of $C_1$-$C_6$ alkyl and $C_1$-$C_6$ alkoxy; X represents linear or branched $C_1$-$C_{20}$ alkyl or aryl substituted with one or more groups selected from the group consisting of $C_1$-$C_6$ alkyl and $C_1$-$C_6$ alkoxy, optionally substituted with one or more heteroatoms comprising oxygen, nitrogen, and sulfur and reacting the immobilized reactive moieties with the amino group-containing molecule so as to immobilize said molecule on the surface. Devices having a surface with immobilized molecules such as nucleic acids or proteins are useful for detection of target analytes in a sample.

13 Claims, 6 Drawing Sheets

U.S. PATENT DOCUMENTS

| | | | |
|---|---|---|---|
| 6,045,996 A | 4/2000 | Cronin et al. | 435/6 |
| 6,080,585 A | 6/2000 | Southern et al. | 436/94 |
| 6,101,946 A | 8/2000 | Martinsky | 101/494 |
| 6,103,474 A | 8/2000 | Dellinger et al. | 435/6 |
| 6,124,102 A | 9/2000 | Fodor et al. | 435/7.1 |
| 6,136,269 A | 10/2000 | Winkler et al. | 422/61 |
| 6,140,044 A | 10/2000 | Besemer et al. | 435/6 |
| 6,141,096 A | 10/2000 | Stern et al. | 356/318 |
| 6,146,593 A | 11/2000 | Pinkel et al. | 422/68.1 |
| 6,150,103 A | 11/2000 | Ness et al. | 435/6 |
| 6,150,147 A | 11/2000 | Goldberg et al. | 435/173.1 |
| 6,153,743 A | 11/2000 | Hubbell et al. | 536/25.3 |
| 6,174,683 B1 | 1/2001 | Hahn et al. | 435/6 |
| 6,180,942 B1 | 1/2001 | Tracey et al. | 250/299 |
| 6,203,989 B1 | 3/2001 | Goldberg et al. | 435/6 |
| 6,225,625 B1 | 5/2001 | Pirrung et al. | 250/302 |
| 6,239,273 B1 | 5/2001 | Pease et al. | 536/25.3 |
| 6,248,127 B1 | 6/2001 | Shah et al. | 623/1.15 |
| 6,261,776 B1 | 7/2001 | Pirrung et al. | 435/6 |
| 6,262,216 B1 | 7/2001 | McGall | 528/10 |
| 6,271,957 B1 | 8/2001 | Quate et al. | 359/298 |
| 6,274,384 B1 | 8/2001 | Starzl et al. | 436/518 |
| 6,280,950 B1 | 8/2001 | Lipshutz et al. | 435/6 |
| 6,284,465 B1 | 9/2001 | Wolber et al. | 435/6 |
| 6,284,497 B1 | 9/2001 | Sabanayagam et al. | 435/91.2 |
| 6,291,183 B1 | 9/2001 | Pirrung et al. | 435/6 |
| 6,294,324 B1 | 9/2001 | Bensimon et al. | 435/6 |
| 6,306,584 B1 | 10/2001 | Bamdad | 435/6 |
| 6,309,824 B1 | 10/2001 | Drmanac | 435/6 |
| 6,309,828 B1 | 10/2001 | Schleifer et al. | 435/6 |
| 6,319,674 B1 | 11/2001 | Fulcrand et al. | 435/7.1 |
| 6,326,489 B1 | 12/2001 | Church et al. | 536/25.3 |
| 6,329,143 B1 | 12/2001 | Stryer et al. | 435/6 |
| 6,339,147 B1 * | 1/2002 | Lukhtanov et al. | 536/23.1 |
| 6,361,944 B1 | 3/2002 | Mirkin et al. | 435/6 |
| 6,383,742 B1 | 5/2002 | Drmanac et al. | 435/6 |
| 6,383,749 B2 | 5/2002 | Bochkariov et al. | 435/6 |
| 6,399,365 B2 | 6/2002 | Besemer et al. | 435/287.2 |
| 6,403,317 B1 | 6/2002 | Anderson | 435/6 |
| 6,403,957 B1 | 6/2002 | Fodor et al. | 250/302 |
| 6,406,844 B1 | 6/2002 | Pirrung et al. | 435/6 |
| 6,406,921 B1 | 6/2002 | Wagner et al. | 436/518 |
| 6,410,229 B1 | 6/2002 | Lockhart et al. | 435/6 |
| 6,410,675 B2 | 6/2002 | McGall et al. | 528/10 |
| 6,417,340 B1 | 7/2002 | Mirkin et al. | 536/23.1 |
| 6,417,506 B1 | 7/2002 | Pinkel et al. | 250/216 |
| 6,429,275 B2 | 8/2002 | McGall et al. | 528/10 |
| 6,440,677 B2 | 8/2002 | Lipshutz et al. | 435/6 |
| 6,448,010 B1 | 9/2002 | Zhao | 435/6 |
| 6,458,533 B1 | 10/2002 | Felder et al. | 435/6 |
| 6,465,178 B2 | 10/2002 | Chappa et al. | 435/6 |
| 6,475,440 B1 | 11/2002 | Bochkariov | 422/100 |
| 6,475,808 B1 | 11/2002 | Wagner et al. | 436/518 |
| 6,475,809 B1 | 11/2002 | Wagner et al. | 436/518 |
| 6,480,324 B2 | 11/2002 | Quate et al. | 359/298 |
| 6,482,593 B2 | 11/2002 | Walt et al. | 435/6 |
| 6,486,287 B2 | 11/2002 | McGall et al. | 528/10 |
| 6,489,160 B2 | 12/2002 | Hashimoto | 435/287.2 |
| 6,498,010 B1 | 12/2002 | Fitzgerald et al. | 435/6 |
| 6,506,895 B2 | 1/2003 | Guire et al. | 536/25.32 |
| 6,511,849 B1 | 1/2003 | Wang | 436/47 |
| 6,514,768 B1 | 2/2003 | Guire et al. | 436/518 |
| 6,548,021 B1 | 4/2003 | Church et al. | 422/68.1 |
| 6,548,257 B2 | 4/2003 | Lockhart et al. | 435/6 |
| 6,548,263 B1 | 4/2003 | Kapur et al. | |
| 6,548,652 B2 | 4/2003 | Lukhtanov et al. | |
| 6,551,817 B2 | 4/2003 | Besemer et al. | 435/287.2 |
| 6,562,136 B1 | 5/2003 | Chappa et al. | 118/500 |
| 6,569,671 B1 | 5/2003 | Okamoto et al. | 435/285.1 |
| 6,579,463 B1 | 6/2003 | Winningham et al. | 216/41 |
| 6,579,719 B1 | 6/2003 | Hutchens et al. | 436/161 |
| 6,589,778 B1 | 7/2003 | Hawkins | 435/287.2 |
| 6,605,363 B2 | 8/2003 | Ho et al. | 428/448 |
| 6,617,125 B2 | 9/2003 | Adler, Jr. | 435/28 |
| 6,621,553 B2 | 9/2003 | Baxter et al. | 355/26 |
| 6,630,308 B2 | 10/2003 | Stryer et al. | 435/6 |
| 6,630,358 B1 | 10/2003 | Wagner et al. | 436/518 |
| 6,632,605 B1 | 10/2003 | Cronin et al. | 435/6 |
| 6,646,243 B2 | 11/2003 | Pirrung et al. | 250/200 |
| 6,660,234 B2 | 12/2003 | Stryer et al. | 422/131 |
| 6,667,394 B2 | 12/2003 | Pease et al. | 536/25.3 |
| 6,680,178 B2 | 1/2004 | Harris et al. | 435/23 |
| 6,703,498 B2 | 3/2004 | Tchaga | 536/112 |
| 6,706,408 B2 | 3/2004 | Jelle | 428/447 |
| 6,709,712 B2 | 3/2004 | Chappa et al. | 427/425 |
| 6,713,262 B2 | 3/2004 | Gellibolian et al. | 435/6 |
| 6,733,894 B2 | 5/2004 | Ho et al. | 428/451 |
| 6,733,977 B2 | 5/2004 | Besemer et al. | 435/6 |
| 6,741,344 B1 | 5/2004 | Stern et al. | 536/317 |
| 6,743,630 B2 | 6/2004 | Sato | 435/402 |
| 6,743,882 B2 | 6/2004 | McGall et al. | 528/10 |
| 6,747,143 B2 | 6/2004 | Stryer et al. | 536/23.1 |
| 6,753,145 B2 | 6/2004 | Holcomb et al. | 435/6 |
| 6,756,232 B1 | 6/2004 | Schermer et al. | 436/180 |
| 6,762,019 B2 | 7/2004 | Swan et al. | 435/6 |
| 6,773,676 B2 | 8/2004 | Schembri | 422/102 |
| 6,773,888 B2 | 8/2004 | Li et al. | 435/6 |
| 6,777,239 B2 | 8/2004 | Dower et al. | 436/6 |
| 6,784,982 B1 | 8/2004 | Blumenfeld et al. | 356/71 |
| 6,794,197 B1 | 9/2004 | Indermuhle et al. | 436/174 |
| 6,797,393 B2 | 9/2004 | Qiao et al. | 428/478.2 |
| 6,800,849 B2 | 10/2004 | Staats | 250/288 |
| 6,806,047 B2 | 10/2004 | Goldberg et al. | 435/6 |
| 6,806,050 B2 | 10/2004 | Zhou et al. | 435/6 |
| 6,808,908 B2 | 10/2004 | Yao et al. | 435/181 |
| 6,811,969 B1 | 11/2004 | Hutchens et al. | 435/5 |
| 6,818,394 B1 | 11/2004 | O'Donnell-Maloney et al. | 435/6 |
| 6,818,411 B2 | 11/2004 | Hutchens et al. | 435/7.2 |
| 6,828,104 B2 | 12/2004 | Lipshutz et al. | 435/6 |
| 6,828,110 B2 | 12/2004 | Lee et al. | 435/7.1 |
| 6,844,165 B2 | 1/2005 | Hutchens et al. | 435/7.92 |
| 6,849,462 B1 | 2/2005 | Winkler et al. | 436/180 |
| 6,852,393 B2 | 2/2005 | Gandon | 428/195.1 |
| 6,855,490 B2 | 2/2005 | Sompuram et al. | 435/4 |
| 6,855,501 B2 | 2/2005 | Huang | 435/6 |
| 7,011,940 B1 * | 3/2006 | Sompuram et al. | 435/4 |
| 2001/0031468 A1 | 10/2001 | Chenchik et al. | 435/6 |
| 2001/0031469 A1 | 10/2001 | Volinia | 435/6 |
| 2001/0041249 A1 | 11/2001 | Patron et al. | 435/7.92 |
| 2001/0053521 A1 | 12/2001 | Kramer et al. | 435/6 |
| 2002/0001834 A1 | 1/2002 | Keogh et al. | 435/174 |
| 2002/0019015 A1 | 2/2002 | Lahiri et al. | 435/7.9 |
| 2002/0042048 A1 | 4/2002 | Drmanac | 435/6 |
| 2002/0072127 A1 | 6/2002 | Sofield et al. | 436/518 |
| 2002/0075490 A1 | 6/2002 | Chappell | 358/1.8 |
| 2002/0076716 A1 | 6/2002 | Sabanayagam et al. | 435/6 |
| 2002/0076727 A1 | 6/2002 | Cardone et al. | 435/7 |
| 2002/0094544 A1 | 7/2002 | Fang et al. | 435/7 |
| 2002/0106702 A1 | 8/2002 | Wagner et al. | 435/7.9 |
| 2002/0137090 A1 | 9/2002 | Pinkel et al. | 435/6 |
| 2002/0142351 A1 | 10/2002 | Diamond | 435/7 |
| 2002/0155442 A1 | 10/2002 | Mirkin et al. | |
| 2002/0164656 A1 | 11/2002 | Hoeffler et al. | 435/7 |
| 2003/0013130 A1 | 1/2003 | Charych et al. | 435/7 |
| 2003/0027154 A1 | 2/2003 | Narahara et al. | 435/6 |
| 2003/0027298 A1 | 2/2003 | Bott et al. | 435/183 |
| 2003/0032035 A1 | 2/2003 | Chatelain et al. | 435/6 |
| 2003/0036095 A1 | 2/2003 | Tchaga | 435/7 |
| 2003/0040129 A1 | 2/2003 | Shah | 436/526 |
| 2003/0044801 A1 | 3/2003 | Harvey | 435/6 |
| 2003/0059094 A1 | 3/2003 | Cattell et al. | 382/128 |
| 2003/0068621 A1 | 4/2003 | Briggs | 435/6 |
| 2003/0099930 A1 | 5/2003 | Graves et al. | 435/5 |

| | | | | |
|---|---|---|---|---|
| 2003/0138853 A1 | 7/2003 | Lahiri et al. | ............... | 435/7 |
| 2003/0143542 A1 | 7/2003 | Qiao et al. | ............... | 435/6 |
| 2003/0143576 A1 | 7/2003 | Chao et al. | ............... | 435/6 |
| 2003/0148360 A1 | 8/2003 | Guire et al. | ............... | 435/6 |
| 2003/0166261 A1 | 9/2003 | Sompuram et al. | ............... | 435/287.2 |
| 2003/0170914 A1 | 9/2003 | Guire et al. | ............... | 436/518 |
| 2003/0180957 A1 | 9/2003 | Koopmann et al. | ............... | 436/56 |
| 2003/0186252 A1 | 10/2003 | Ilsley et al. | ............... | 435/6 |
| 2003/0186310 A1 | 10/2003 | Kincaid et al. | ............... | 435/6 |
| 2003/0198967 A1 | 10/2003 | Matson et al. | ............... | 435/6 |
| 2003/0215806 A1 | 11/2003 | Lewis et al. | ............... | 435/6 |
| 2003/0215841 A1 | 11/2003 | Lockhart et al. | ............... | 435/6 |
| 2003/0215856 A1 | 11/2003 | Church et al. | ............... | 435/6 |
| 2003/0231987 A1 | 12/2003 | Carmack et al. | ............... | 422/99 |
| 2004/0002078 A1 | 1/2004 | Boutell et al. | ............... | 435/6 |
| 2004/0018523 A1 | 1/2004 | Hawkins et al. | ............... | 435/6 |
| 2004/0063220 A1 | 1/2004 | Lebrun | ............... | 436/518 |
| 2004/0029303 A1 | 2/2004 | Hart et al. | ............... | 438/16 |
| 2004/0073017 A1 | 4/2004 | Skrzypcznski et al. | ............... | 536/23 |
| 2004/0076961 A1 | 4/2004 | Lewis et al. | ............... | 435/6 |
| 2004/0096856 A1* | 5/2004 | Garimella et al. | ............... | 435/6 |
| 2004/0096914 A1 | 5/2004 | Fang et al. | ............... | 435/7 |
| 2004/0101838 A1 | 5/2004 | Thompson et al. | ............... | 435/6 |
| 2004/0106131 A1 | 6/2004 | Roy et al. | ............... | 435/66 |
| 2004/0132080 A1 | 7/2004 | Kawaguchi et al. | ............... | 435/287 |
| 2004/0137493 A1 | 7/2004 | Goldberg et al. | ............... | 435/6 |
| 2004/0142095 A1 | 7/2004 | Narahara et al. | ............... | 427/2 |
| 2004/0161748 A1 | 8/2004 | He et al. | ............... | 435/6 |
| 2004/0175717 A1 | 9/2004 | Van Zyle et al. | ............... | 435/6 |
| 2004/0185451 A1 | 9/2004 | Leproust et al. | ............... | 435/6 |
| 2004/0185464 A1 | 9/2004 | Kris et al. | ............... | 435/6 |
| 2004/0185473 A1 | 9/2004 | Cuppoletti et al. | ............... | 435/6 |
| 2004/0191813 A1 | 9/2004 | Bruhn et al. | ............... | 435/6 |
| 2004/0206902 A1 | 10/2004 | Staats et al. | ............... | 250/288 |
| 2004/0209383 A1 | 10/2004 | Yin et al. | ............... | 436/518 |
| 2004/0214019 A1 | 10/2004 | McGall et al. | ............... | 428/447 |
| 2004/0215031 A1 | 10/2004 | McGall et al. | ............... | 556/413 |
| 2004/0224326 A1 | 11/2004 | Kim et al. | ............... | 435/6 |
| 2004/0229287 A1 | 11/2004 | Sato et al. | ............... | 435/7 |
| 2004/0234788 A1 | 11/2004 | Li et al. | ............... | 428/447 |
| 2004/0241663 A1 | 12/2004 | Peck et al. | ............... | 435/6 |
| 2004/0241666 A1 | 12/2004 | Amorese et al. | ............... | 435/6 |
| 2004/0241668 A1 | 12/2004 | Amorese et al. | ............... | 435/6 |
| 2004/0241742 A1 | 12/2004 | Peck et al. | ............... | 435/7 |
| 2004/0241880 A1 | 12/2004 | Leproust et al. | ............... | 436/518 |
| 2004/0248162 A1 | 12/2004 | Cuppoletti et al. | ............... | 435/6 |
| 2004/0248323 A1 | 12/2004 | Zhou et al. | ............... | 436/518 |
| 2004/0253460 A1 | 12/2004 | McGall et al. | ............... | 428/447 |
| 2004/0253640 A1 | 12/2004 | Chen et al. | ............... | 435/7 |
| 2004/0265813 A1 | 12/2004 | Takechi et al. | ............... | 435/6 |
| 2005/0003395 A1 | 1/2005 | Gellibolian et al. | ............... | 435/6 |
| 2005/0008674 A1 | 1/2005 | Wagner et al. | ............... | 424/423 |
| 2005/0014292 A1 | 1/2005 | Wagner et al. | ............... | 436/518 |
| 2005/0032060 A1 | 2/2005 | Shah et al. | ............... | 435/6 |

FOREIGN PATENT DOCUMENTS

| | | |
|---|---|---|
| EP | 0 628 568 | 6/1994 |
| EP | 1 001 267 | 5/2000 |
| WO | WO 91/00288 A1 | 1/1991 |
| WO | WO 98/04740 | 2/1998 |
| WO | WO 99/04896 * | 2/1999 |
| WO | WO 01/00876 | 1/2001 |
| WO | WO 01/46213 | 6/2001 |
| WO | WO 01/46214 | 6/2001 |
| WO | WO 01/46464 | 6/2001 |
| WO | WO 01/51665 | 7/2001 |
| WO | WO 01/51689 | 7/2001 |
| WO | WO 01/98458 | 12/2001 |
| WO | WO 02/06384 | 1/2002 |
| WO | WO 03/006676 | 7/2002 |
| WO | WO 02/096979 | 12/2002 |

OTHER PUBLICATIONS

Lenhart et al. "Immobilizing a Fluorescent Dye Offers Potential to Investigate the Glass/Resin Interface" Journal of Colloid and Interface Science Jan. 2000, 221, 75-86.*

Satchell et al. "Acylation of Ketens and Isocyanates. A Mechanistic Comparison" Chem. Soc. Rev. 1975, 4, 231-250.*

Dickinson et al., "A Novel Probe for Free Radicals featuring Epoxide Cleavage" J. Chem. Soc. Perkin Trans. 1 1990, 1179-1184.*

Beck C., et al., "Covalent surface functionalization and self-organization of silica nanoparticles," *Angew .Chem. Int. Ed*,vol. 38, No. 9, p. 1297-1300 (1999).

Beier M., et al., "Versatile derivatisation of solid support media for covalent bonding on DNA-microchips," *Nucleic Acids Research*, vol. 27, p. 1970-1977 (1999).

Chrisey L., et al., "Covalent attachment of synthetic DNA to self-assembled monolayer films," *Nucleic Acids Research*, vol. 24, p. 3031-3039 (1996).

Chrisey L., et al., "Fabrication of patterned DNA surfaces," *Nucleic Acids Research*, vol. 24, p. 3040-3047 (1996).

Frens, G. "Controlled Nucleation for the Regulation of the Particle Size in Monodisperse Gold Suspensions," *Nature Physical Science*, vol. 241, p. 20-22 (1973).

Eckstein, F. (ed.) *Oligonucleotides and Analogues: A Practical Approach* (IRL Press, Oxford, 1991), pp. vii-xvii.

Grabar K., et al., "Preparation and characterization of au colloid monolayers," *Analytical Chemistry*, vol. 67, p. 735-743 (1995).

Guo Z., et al., "Direct fluorescence analysis of genetic polymorphism by hybridization with oligonucleotide arrays on glass supports," *Nucleic Acids Research*, vol. 22, p. 5456-5465 (1994).

Letsinger R., et al., "Use of a steroid cyclic disulfide anchor in constructing gold nanoparticle-oligonucleotide conjugates," *Bioconjugate Chem*, vol. 11, p. 289-291 (2000).

Zammateo N., et al., "Comparison between different strategies of covalent attachment of DNA to glass surfaces to build DNA microarrays," *Analytical biochemistry*, vol. 280, p. 143-150 (2000).

Zhao X., et al., "Immobilization of oligodeoxyribonucleotides with multiple anchors to microchips," *Nucleic Acids Research*, vol. 29, p. 955-959 (2001).

Highsmith F., et al., "Evaluation of CNBr, FMP and hydrazide resins for immunoaffinity purification of factor IX," *Biotechniques*, vol. 12, p. 418-426 (1992).

Kumar A., et al., "Silanized nucleic acids: a general platform for DNA immobilization," *Nucleic Acids Research*, vol. 28, p. 1-6 (2000).

Lindroos K., et al., "Minisequencing on oligonucleotide microarrays: comparison of immobilization chemistries," *Nucleic Acids Research*, vol. 29, No. 13, p. 1-7 (2001).

Ramsay G., "DNA chips: State-of-the art," *Nature Biotechnology*, vol. 16, p. 40-44 (1998).

Rogers Y., et al., "Immobilization of Oligonucleotides onto a Glass Support via Disulfide Bonds: A Method for Preparation of DNA Microarrays," *Analytical Biochemistry*, vol. 266, p. 23-30 (1999).

Weetall, Howard H., "Preparation of Immobilized Proteins Covalently Coupled Through Silane Coupling Agents to Inorganic Supports," *Applied Biochemistry and Biotechnology*, vol. 41, p. 157-188 (1993).

Material Safety Data Sheet for Aliphatic Isocyanate, 2005.

Parker, Anthony A., "A Technical Review of Organosilanes and Adhesion", 2001.

Pierce Biotechnology, Instructions for EDC, May 2002.

Spanne, Mårten, "Derivatization and Analysis of Aromatic Iscyanates with Dibutylamine and Liquid Chromatography", Lund Institute of Technology, Lund University, Publication 47, ISSN 1104-1080, 1998.

Weetall, H. H., "Covalent Coupling Methods for Inorganic Support Materials", *Methods in Enzymology*, 1976, vol. 44, pp. 134-139.

Sompuram et al., Anal. Biochem., vol. 326, pp. 55-68 (2004).

Beyer, et al., *Langmuir* 1996, 12, p. 2514-2518.

Walsh et al., *J. Biochem. Biophys. Methods* 47, p. 221-231 (2001).

Sompuram et al., *Journal of Histochemistry and Cytochemistry*, vol. 50, p. 1425-1433 (2002).

Sompuram et al., *Clinical Chemistry* 48:3, p. 410-420 (2002).

Sompuram et al., *Journal of Histotechnology*, vol. 26, No. 2, p. 117-123 (2003).

Guo, Z. et al., "Direct fluorescence analysis of genetic polymorphisms by hybridization with oligonucleotide arrays on glass supports", *Nucleic Acid Research*, 1994, vol. 22, No. 24, 5456-5465.

Anspach et al., *Analytical Biochemistry*, vol. 179, pp. 171-181 (1989).

Huckel et al., *J. Biochem. Biophys. Methods*, vol. 31, pp. 165-179 (1996).

Wieser et al., *J. Biochem. Biophy. Methods*, vol. 15, pp. 13-22 (1987).

Ghosh et al., Covalent attachment of oligonucleotides to solid supports, Nucleic Acids Research, 1987, pp. 5353-5372, vol. 15, No. 13, IRL Press Limited, Oxford, England.

Kolchinsky et al., Analysis of SNPs and Other Genomic Variations Using Gel-Based Chips, Human Mutation, 2002, vol. 19, pp. 343-360, published online in Wiley InterScience (www.interscience.wiley.com).

Nature Genetics (supplement), Jan. 1999, pp. 1-60, vol. 21, No. 1, Nature America Inc., New York, New York, USA.

Gill et al., "Degradation of Organophosphorous Nerve Agents by Enzyme-Polymer Nanocomposites: Efficient Biocatalytic Materials for Personal Protection and Large-Scale Detoxification", *Biotechnology and Bioengineering*, Nov. 20, 2000, pp. 400-410, vol. 70, No. 4, John Wiley & Sons.

* cited by examiner

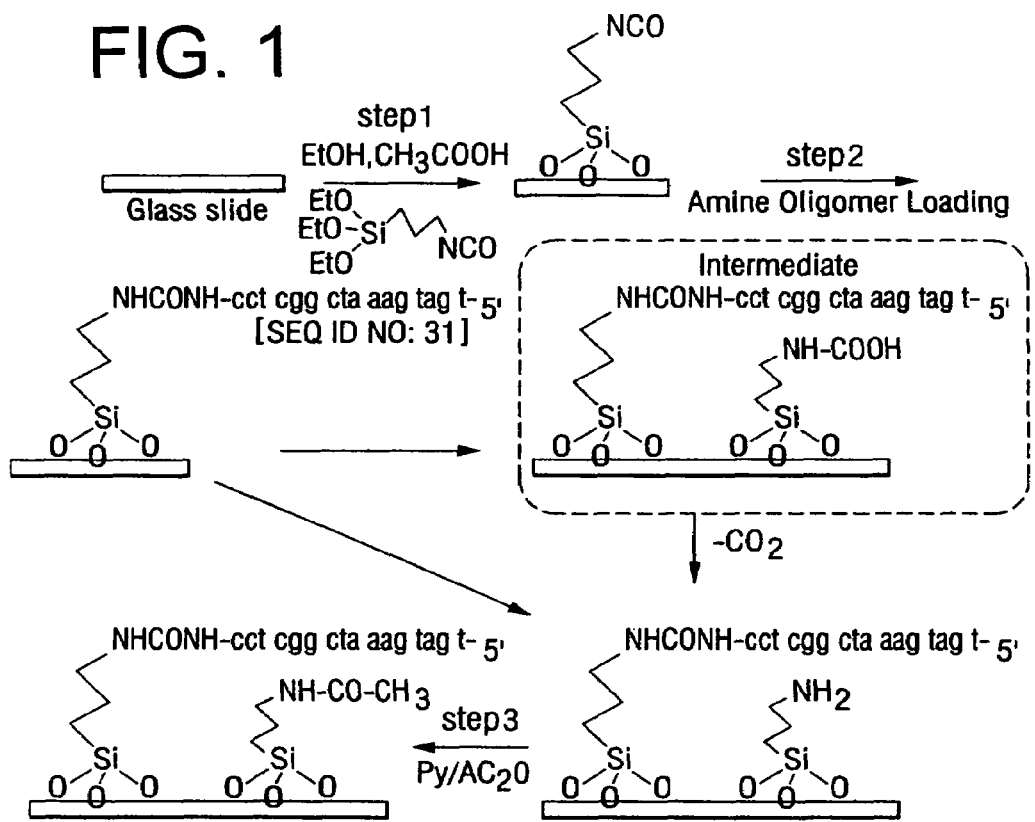
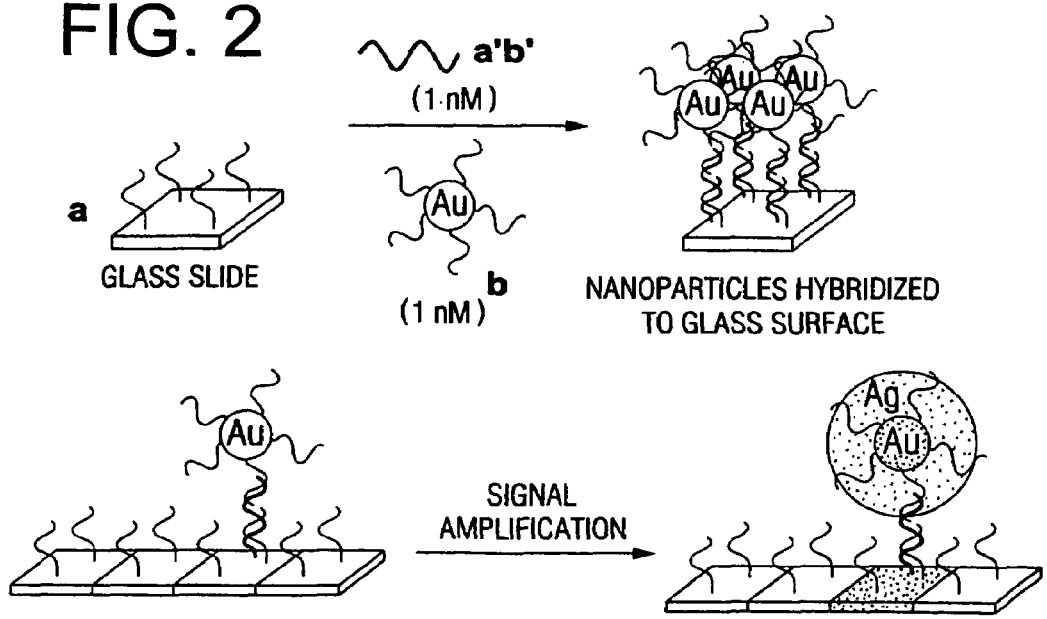

METHOD FOR IMMOBILIZING MOLECULES ONTO SURFACES

CROSS-REFERENCE

This application claims the benefit of U.S. Provisional application Nos. 60/305,369, filed Jul. 13, 2001 and 60/363,472, filed Mar. 12, 2002, which are incorporated by reference in its entirety.

FIELD OF THE INVENTION

The present invention relates to a method for immobilizing amino-group containing molecules such as nucleic acids, proteins, carbohydrates onto surfaces that have immobilized isocyanate groups bound thereto. The invention also relates to devices having bound thereto isocyanate groups or molecules including probes or linkers for attaching other molecules or probes.

BACKGROUND OF THE INVENTION

DNA attachment to glass surfaces has become an important tool in the genomics industry for many applications, including gene expression analysis and DNA detection methods. In general, DNA can be attached to glass either through non-covalent, ionic interactions, or through covalent multi-step processes or simple covalent coupling reactions. The reported methods, however, involve labor intensive, expensive and potentially hazardous steps in some methods.

The present invention provides a simple, fast, and inexpensive method to covalently attach synthetic DNA and other molecules directly or in a stepwise manner to a derivatized surface having immobilized isocyanate groups and devices having surfaces prepared by the inventive method. The inventive method can be extended to covalently attach proteins, amino acids, carbohydrates, lipids and other molecules to surfaces, such as a glass surface. Surfaces modified through attachment of nucleic acids, amino acids, proteins, carbohydrates, lipids and other molecules using the present inventive method are useful in diagnostic applications for screening for the presence or absence of target molecules in samples.

SUMMARY OF THE INVENTION

The present invention relates to a method for attaching amino-group containing molecules such as nucleic acids, amino acids, proteins, and carbohydrates or other amino-containing molecules that have been derivatized with one or more amino groups to a surface such as a glass surface that has been reacted with a silyl isocyanate derivatizing agent. For instance, the method can be used to attach a 3' or 5' amino-derivatized end of DNA extracted from cells or synthesized by conventional procedures in a direct or indirect manner to a support having a glass surface or other surfaces with free hydroxyl groups. It is known that one cannot couple amino-group containing molecules to a glass surface very easily. One advantage of the inventive method is that it overcomes this problem by first immobilizing isocyanate groups that can react very fast with amines and form stable amide linkages. Moreover, amino group containing DNA molecules can be readily immobilized onto immobilized isocyanates on the surface, even in the presence of aqueous buffer. The resulting isocyanate modified glass surface having amide-linked DNA or other molecules bound thereto are highly stable in enzymatic, acidic and basic conditions.

Accordingly, one embodiment of the invention provides a method for immobilizing an amino-group containing molecule on a surface having free hydroxyl groups. The method comprises the steps of:

(a) reacting the free hydroxyl groups of said surface with a silyl isocyanate derivatizing agent to provide immobilized reactive moieties, the agent having a formula:

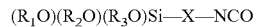

$(R_1O)(R_2O)(R_3O)Si—X—NCO$ wherein $R_1$, $R_2$ and $R_3$ independently represents $C_1$-$C_6$ alkyl, phenyl, or aryl substituted with one or more groups selected from the group consisting of $C_1$-$C_6$ alkyl and $C_1$-$C_6$ alkoxy; X represents linear or branched $C_1$-$C_{20}$ alkyl or aryl substituted with one or more groups selected from the group consisting of $C_1$-$C_6$ alkyl and $C_1$-$C_6$ alkoxy, optionally substituted with one or more heteroatoms comprising oxygen, nitrogen, and sulfur; and (b) reacting the immobilized reactive moieties with the amino-group containing molecule so as to immobilize said molecule on the surface.

In another aspect of this embodiment of the invention, the method for immobilizing the molecule further comprises the steps of:

(c) reacting the immobilized molecule on the surface with a chemical agent that reacts with the functional group of the molecule so as to produce second immobilized reactive moieties; and (d) reacting the second immobilized reactive moieties with a second molecule having a functional group capable of reacting with the second immobilized reactive moieties.

In another embodiment of the invention, the method further comprises the step of:

(c) coupling the molecule immobilized on the surface with a second molecule, wherein the molecule immobilized on the surface and the second molecules have at least one functional group for coupling.

In another embodiment of the invention, a method for immobilizing a probe on a glass surface is provided. The method comprises the steps of:

(a) reacting the glass surface with (3-isocyanatopropyl) triethoxysilane to provide immobilized reactive moieties; and (b) reacting the immobilized reactive moieties with a molecule having an amine group so as to immobilize said molecule on the glass surface.

In yet another aspect of the invention, the method further comprises the steps of:

(c) reacting the immobilized molecule on the surface with a chemical agent that reacts with the functional group of the molecule so as to produce second immobilized reactive moieties; and (d) reacting the second immobilized reactive moieties with a second molecule having a functional group capable of reacting with the second immobilized reactive moieties.

In another embodiment of the invention, the present invention provides devices comprising a surface with an immobilized molecule prepared by the inventive method. These and other embodiments of the invention will become apparent in light of the detailed description below.

IN THE DRAWINGS

FIG. 1 provides a schematic diagram of DNA attachment on isocyanate plates (see Example 1).

FIG. 2 is a general illustration that uses gold nanoparticle probes as detection labels for detecting for the presence of a target DNA molecule using capture probes bound to the inventive plates having isocyanate groups attached thereto. The nanoparticle-oligonucleotide conjugate detections probes have oligonucleotides (b) bound thereto for detection of target a'b' using a glass DNA chip having capture probe oligonucleotides (a). The sequence of the oligonucleotides (b) bound to the nanoparticles are complementary to a portion (b') of the sequence of target a'b' while the sequence of the capture oligonucleotides (a) bound to the glass chip are complementary to another portion (a') of the target a'b' sequence. See Example 2.

Figure 12:
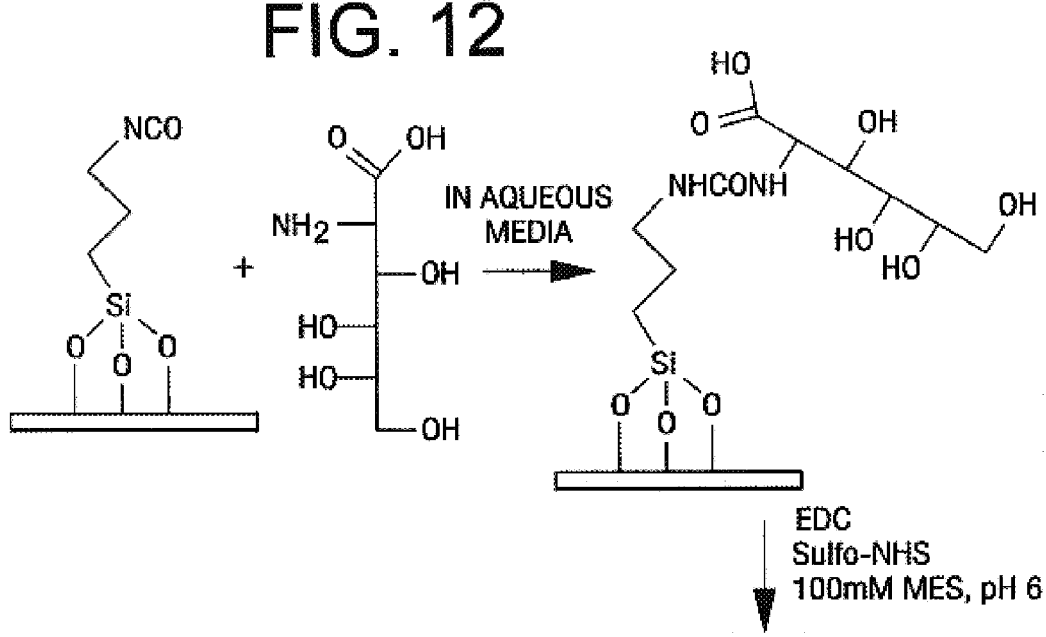

FIG. 12 is a schematic diagram illustrating the stepwise modification of the glass plate. Amino-group containing sugar molecules in aqueous solution were reacted with the isocyanate linked glass surface to immobilize the sugar molecule onto the plate. Thereafter, a second molecule including a functional group (an amino-group containing DNA capture probe) is coupled to the first molecule immobilized onto the surface in the presence of a coupling agent such as EDC. See Example 8.

Figure 13:
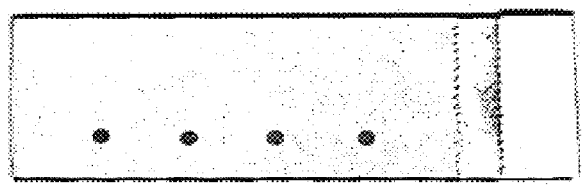

FIG. 13 illustrates MTHFR 100mer synthetic sequence detection on carbohydrate modified plate from Example 8.

Figure 14:
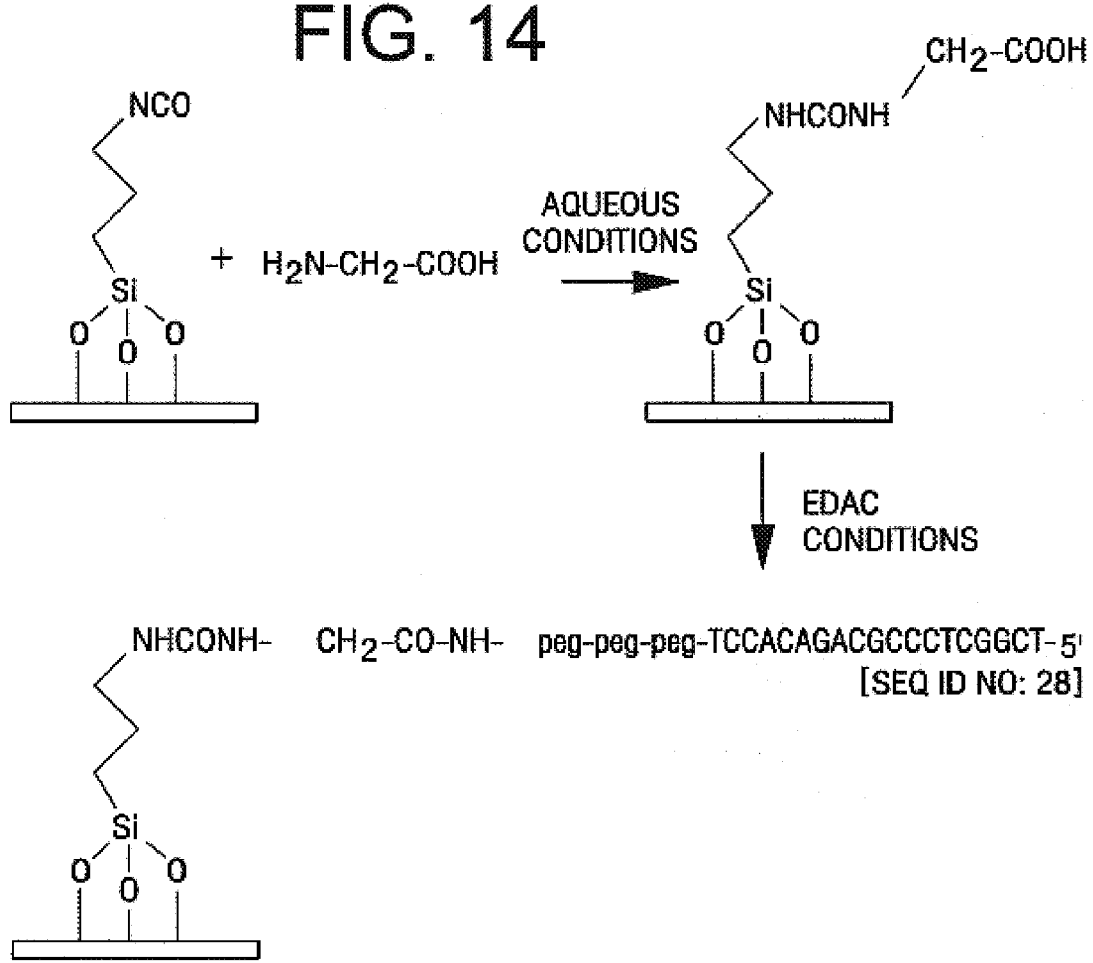

FIG. 14 illustrates a schematic diagram for the stepwise attachment of a DNA capture probe via amino acid linker to an isocyanate modified glass plate. Amino acid molecules in aqueous solution were reacted with the isocyanate linked glass surface to immobilize the amino acid onto the plate. Thereafter, a second molecule including a functional group (an amino-group containing DNA capture probe) is coupled to the first molecule immobilized onto the surface in the presence of a coupling agent such as EDAC. See Example 9.

Figure 15:
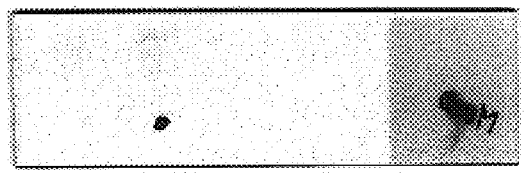

FIG. 15 illustrates MTHFR 100mer synthetic sequence detection on amino acid modified plate from Example 9.

DETAILED DESCRIPTION OF THE INVENTION

The present invention provides a method for the covalent attachment of molecules such as amino-group containing nucleic acids, amino acids, proteins, carbohydrates, or other molecules derivatized with amino groups to an isocyanate modified surface and devices having a surface with immobilized molecules prepared by the inventive method.

One aspect of the invention relates to the immobilization of a molecule having amino-groups onto surfaces having reactive hydroxyl groups such as siliconized surfaces, germanium surfaces, mica, silicon wafers, wave guides, nylon and silicon dioxide glass surfaces. In practicing this invention, substrates having glass surfaces, e.g., glass slides or beads, are preferred. FIGS. 1, 12 and 14 illustrates the basic reactions involved in the immobilization process using a silyl isocyanate derivatizing agent for derivatizing the glass surface. The silyl isocyanate derivatizing agent has the following formula:

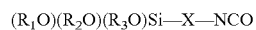

$(R_1O)(R_2O)(R_3O)Si-X-NCO$ wherein $R_1$, $R_2$ and $R_3$ are independently $C_1$-$C_6$ alkyl; X represents a $C_1$-$C_{20}$ linear or branched alkyl group optionally substituted with one or more heteroatoms such ascarbon, hydrogen, nitrogen, sulfur, and oxygen. In practicing this invention, (3-isocyanatopropyl) triethoxysilane is preferred as the silyl isocyanate derivatizing agent.

Any type of glass surface may be used as a substrate, including glass slides or beads, provided that it is adequately cleaned prior to derivatization. Washing with acid, followed by successive washings in water and organic solvents has been found to produce adequate results.

The cleaned dried glass surface is reacted (e.g., 1.5 hours at room temperature) with a silyl isocyanate dissolved in a suitable solvent mixture comprised of organic solvent and an acid. Suitable, but non-limiting, examples of solvent include alcohols such as absolute ethanol, methanol, and propanol; toluene; tetrahydrofuran; and dimethyl sulfoxide. Suitable acids include glacial acetic acid, hydrochloric acid and sulfuric acid. The amount of acid in the mixture generally ranges from between about 0.01% (v/v) and about 0.1%(v/v), preferably about 0.01% (v/v). In practicing this invention, absolute ethanol is preferred as organic solvent and glacial acetic acid is preferred as acid at a ratio of ranging between about 1:0.0001 to about 1:0.001, preferably about 100000:1 v/v ethanol/glacial acetic acid. The concentration of the silyl isocyanate generally ranges between about 20 mM and about 200 mM, preferably about 80 mM.

Glass surfaces containing immobilized reactive groups are then washed with a suitable organic solvent to remove unreacted silyl isocyanate. Representative examples of suitable solvents include toluene, acetone, and ethanol. The washed plates are then dried (e.g., at room temperature for 5-10 minutes). The glass surface may be kept dry by storage in a vacuum desiccator prior to use.

Surface-bound isocyanate moieties present on the glass surface react with the amino groups of amino-group containing molecules such as amino-derivatized oligonucleotides to form a stable urea linkage. In the case of immobilized isothiocyanate moities, attachment occurs through covalent thiourea linkages. Generally, the molecules containing amino groups are dissolved in a suitable solvent such as ethanol, dimethyl sulfoxide, dimethyl form amide, tetrahedrofuran in the optional presence of water. In the case where the molecules are not readily soluble or are insoluble in organic solvent, water may be used alone as the solvent or in combination with a water miscible solvent to enhance the molecule solubility.

The amount of water in aqueous solvent mixtures generally ranges between about 1%(v/v) and about 10% (v/v), preferably about 5%(v/v) in solution having amino-group containing molecules. While any desired concentration of molecule solution may be used, generally the concentration of the amino-group containing molecules generally ranges between about 1 uM and about 2 mM, preferably between about 5 uM and about 1 mM, and most preferably between about 10 uM and about 1 mM. The solution containing molecules having amino groups may applied to the glass surfaces containing the isocyanate immobilized reactive groups by any suitable means, including spotting or spraying. Reactions may be successfully performed at room temperature and are essentially complete within 30 minutes. After completion, the glass slides were washed with water and ethanol and dried. The unreacted isocyanates present on the glass surface are converted into free amines during water washing and these free amines may be blocked using any suitable capping solution, e.g., 1:1 (v/v) pyridine-acetic anhydride mixture. Generally, the capping reaction is conducted for at least 30 minutes, preferably about one hour, at room temperature. After capping the free amines, the plates having immobilized molecules were washed again with ethanol thoroughly and dried in the desiccator until further use.

After attachment of the molecules containing amino groups to the surface, devices having a glass surface prepared in the manner described above can be used in assays for detection purposes where the amino-group containing molecule is a probe. Suitable, but non-limiting examples of probes include a protein, a peptide, a nucleic acid, an amino acid, a peptide nucleic acid, a linked nucleic acid, a nucleoside triphosphate, a carbohydrate, a lipid, a lipid bound protein, an aptamer, a virus, a cell fragment, or a whole cell. The probe may have one or more amino groups inherently as part of its structure or may be derivatized by any suitable means to include one or more amino-groups. In cases where an amino-containing oligonucleotide was used to prepare a device using the above method, the resulting immobilized oligonucleotides may be used in hybridization reactions with other nucleic acids. It has been found that oligonucleotide probes immobilized in the manner described above retain the ability to specifically recognize and bind target DNAs having complementary nucleotide sequences. Assay conditions may be varied to accomplish specific experimental objectives. For example, hybridization assays may be performed at different stringencies depending upon the extent to which the experimenter wants hybridization to occur to target nucleic acids having mismatched nucleotide sequences.

In another aspect of the invention, the immobilized molecules bound to the glass surface may include a functional group, e.g., a carboxyl moiety. This functional group may be used to couple with a second molecule or probe. Hence, the immobilized molecule may act as a spacer or a linker to bind the second molecule or probe to the glass surface. The second molecule includes a second functional group, e.g, amino group, that allows it to react directly or indirectly with the immobilized molecules. Any suitable coupling agents may be used. For instance, FIGS. 12 and 14 illustrate the coupling immobilization of an amino-containing sugar molecule or amino acid, respectively, with the isocyanate modified surface. The amino acid and sugar molecules includes a carboxylic acid moieties which, in the presence of EDC or EDAC or other suitable coupling reagent, convert to a reactive ester intermediate. This ester intermediate couples with an amino-containing oligonucleotide as the second molecule. In practicing this invention, any desired amino-group containing molecule may be used as a linker or spacer, provided that it has some functionality that allows the molecule to covalent attach to another molecule, alone or in the presence of one or more coupling agents. Any suitable concentration of second molecules may be used in any suitable solvent or solvent mixture as described above. Similarly, any suitable method of applying the solution including the second molecules may be used as described above.

In yet another aspect of the invention, devices having glass surfaces modified by the inventive method are provided. In one embodiment of the invention, the device comprises a substrate with a glass surface having bound thereto one or more types of capture probes for immobilizing target analytes contained in a sample onto said substrate, each capture probe specific for a target analyte. In cases where a plurality of different types of capture probes attached are attached to the glass substrate, the capture probes may be arranged as an array to allow for the detection of multiple types of target analytes.

EXAMPLES

The Examples below illustrate those oligonucleotides having amino groups at the 3' or 5' terminal ends can be readily immobilized onto glass surfaces having immobilized reactive isocyanate groups.

The Examples below describe a procedure for the preparation of an isocyanate-linked glass plates (Example 1), attachment of an amino-group containing oligonucleotides onto the isocyanate-linked glass plate (Example 2), and detection of various M-13 phage target molecules nucleic acid sequences using the glass plates having immobilized DNA (capture probes) modified glass plate, and gold nanoparticle-oligonucleotide conjugates as detection probes (Example 2); detection of various MTHFR target nucleic acid sequences using glass plates having immobilized oligonucleotide capture probes and gold nanoparticle conjugates as detection probes; (Examples 3, 6 and 7). Example 4 shows direct hybridization of a gold nanoparticle-oligonucleotide conjugate to a capture oligonucleotide probe immobilized onto the isocyanate plate. Example 5 illustrates detection of Factor V target nucleic acid using glass plates having immobilized oligonucleotide capture probes and gold nanoparticle conjugates as detection probes. Example 8 describes attachment of a amino-group containing carbohydrate linker to an isocyanate plate and subsequent attachment of a nucleic acid molecule to the immobilized linker and the use of the nucleic acid modified plate for detection of a target nucleic acid molecule. Example 9 describes attachment of an amino acid linker to an isocyanate plate and subsequent attachment of a nucleic acid molecule to the linker and the use of the nucleic acid modified plate for detection of a target nucleic acid molecule. Examples 8 and 9 showed coupling of nucleic acid to carbohydrate and amino acid to confirm the presence of the linker on the glass surface.

Example 1

Preparation of Immobilized Isocyanate Plates and DNA Loading

This Example illustrates the general preparation of an isocyanate-linked glass surface and subsequent reaction of an amino-group containing molecule (e.g., a 3' amino DNA molecule). FIG. 1 illustrates the basic steps in generating the reactive isocyanate groups on a surface having free reactive hydroxyl groups and subsequent coupling of an amino-group containing DNA molecule.

(a) Preparation of isocyanate plates: To 100 ml of absolute ethanol (200 proof ACS/USP grade, pharmco products Inc) contained in a polypropylene plastic container, 2 ml of (3-Isocyanatopropyl) triethoxy silane (Sigma Company, St. Louis, Mo., USA; Product no: 58810) and 10 µl of glacial acetic acid was added and the mixture was stirred for one minute. Immediately thereafter, PIRANHA (3:1 $H_2SO_4$: H2O2) cleaned glass slide plates were immersed in the mixture and kept at room temperature for 1.5 h. The glass plates were then washed with ethanol and dried prior to DNA loading.

(b) Preparation of DNA plates: A 12 µM DNA solution was used to cover the dried isocyanate plates and the plates where then kept overnight in a covered box to avoid evaporation of the DNA solution. The amino-containing DNA molecules were prepared as described above. The DNA solution was prepared in 1:9 10 mM Phosphate buffer: DMF mix. The DNA coated plates were then washed with water and ethanol and dried. The unreacted isocyanates that converted into amines during the water washing were treated with a solution of pyridine-acetic anhydride [1:1 ratio, total 100 ml] for 30 minutes at room temperature. In this case where gold nanoparticles were used for detection, amine capping becomes necessary to avoid undesirable chemical reaction between the free amines and the gold surfaces. The plates are then washed with water, then ethanol, and then air dried at room temperature and used for detection.

Example 2

M-13 Target Detection Using Gold Nanoparticles

In this example, capture probes where attached to a glass surface in accordance with the DNA loading procedure in Example 1. Gold nanoparticle-oligonucleotide probes to detect for the target M-13 sequence was prepared using procedures described in PCT/U.S.97/12783, filed Jul. 21, 1997; PCT/US00/17507, filed Jun. 26, 2000; PCT/U.S.01/01190, filed Jan. 12, 2001, which are incorporated by reference in their entirety. FIG. 2 illustrates the use of gold nanoparticle probes having oligonucleotides (b) bound thereto for detection of target a'b' using a glass DNA chip having capture probe oligonucleotides (a). The sequence of the oligonucleotides (b) bound to the nanoparticles are complementary to a portion (b') of the sequence of target a'b' while the sequence of the capture oligonucleotides (a) bound to the glass chip are complementary to another portion (a') of the target a'b' sequence. Under hybridization conditions, the nanoparticle probes, the capture probes and the target sequence bind to form a complex. Signal detection of the resulting complex can be enhanced with conventional silver staining.

(a) Preparation of Gold Nanoparticles

Gold colloids (13 nm diameter) were prepared by reduction of $HAuCl_4$ with citrate as described in Frens, 1973, *Nature Phys. Sci.*, 241:20 and Grabar, 1995, *Anal. Chem.* 67: 735. Briefly, all glassware was cleaned in aqua regia (3 parts HCl, 1 part $HNO_3$), rinsed with Nanopure $H_2O$, then oven dried prior to use. $HAuCl_4$ and sodium citrate were purchased from Aldrich Chemical Company. Aqueous $HAuCl_4$ (1 mM, 500 mL) was brought to reflux while stirring. Then, 38.8 mM sodium citrate (50 mL) was added quickly. The solution color changed from pale yellow to burgundy, and refluxing was continued for 15 min. After cooling to room temperature, the red solution was filtered through a Micron Separations Inc. 1 micron filter. Au colloids were characterized by UV-vis spectroscopy using a Hewlett Packard 8452A diode array spectrophotometer and by Transmission Electron Microscopy (TEM) using a Hitachi 8100 transmission electron microscope. Gold particles with diameters of 13 nm will produce a visible color change when aggregated with target and probe oligonucleotide sequences in the 10-35 nucleotide range.

(b) Synthesis of Oligonucleotides

An oligonucleotide complementary to a segments of the M-13 DNA sequence were synthesized on a 1 micromole scale using a Milligene Expedite DNA synthesizer in single column mode using phosphoramidite chemistry. Eckstein, F. (ed.) *Oligonucleotides and Analogues: A Practical Approach* (IRL Press, Oxford, 1991). All solutions were purchased from Milligene (DNA synthesis grade). Average coupling efficiency varied from 98 to 99.8%, and the final dimethoxytrityl (DMT) protecting group was not cleaved from the oligonucleotides to aid in purification.

To facilitate hybridization of the probe sequence with the target, a deoxyadenosine oligonucleotide ($da_{20}$) was included on the 5' end in the probe sequence as a spacer. Additional $da_{20}$ oligomers were generated as "filler oligonucleotides," comprising a 5'-steroid disulfide unit. These "fillers" further facilitated hybridization with a target by increasing the separation of the recognition oligonucleotide strands anchored on the gold nanoparticles as described below.

To generate 5'-terminal steroid-cyclic disulfide oligonucleotide derivatives (see Letsinger et al., 2000, *Bioconjugate Chem.* 11:289-291 and PCT/U.S.01/01190 (Nanosphere, Inc.), the disclosure of which is incorporated by reference in its entirety), the final coupling reaction was carried out with a cyclic dithiane linked epiandrosterone phosphoramidite on Applied Biosystems automated synthesizer, a reagent that prepared using 1,2-dithiane-4,5-diol, epiandrosterone and p-toluenesulphonic acid (PTSA) in presence of toluene. The phosphoramidite reagent may be prepared as follows: a solution of epiandrosterone (0.5 g), 1,2-dithiane-4,5-diol (0.28 g), and p-toluenesulfonic acid (15 mg) in toluene (30 mL) was refluxed for 7 h under conditions for removal of water (Dean Stark apparatus); then the toluene was removed under reduced pressure and the reside taken up in ethyl acetate. This solution was washed with water, dried over sodium sulfate, and concentrated to a syrupy reside, which on standing overnight in pentane/ether afforded a steroid-dithioketal compound as a white solid (400 mg); Rf (TLC, silica plate, ether as eluent) 0.5; for comparison, Rf values for epiandrosterone and 1,2-dithiane-4,5-diol obtained under the same conditions are 0.4, and 0.3, respectively. Recrystallization from pentane/ether afforded a white powder, mp 110-112° C.; $^1$H NMR, δ 3.6 (1H, $C^3OH$), 3.54-3.39 (2H, m 2OCH of the dithiane ring), 3.2-3.0 (4H, m $2CH_2S$), 2.1-0.7 (29H, m steroid H); mass spectrum ($ES^+$) calcd for $C_{23}H_{36}O_3S_2$ (M+H) 425.2179, found 425.2151. Anal. ($C_{23}H_{37}O_3S_2$) S: calcd, 15.12; found, 15.26. To prepare the steroid-disulfide ketal phosphoramidite derivative, the steroid-dithioketal (100 mg) was dissolved in THF (3 mL) and cooled in a dry ice alcohol bath. N,N-diisopropylethylamine (80 µL) and β-cyanoethyl chlorodiisopropylphosphoramidite (80 µL) were added successively; then the mixture was warmed to room temperature, stirred for 2 h, mixed with ethyl acetate (100 mL), washed with 5% aq. $NaHCO_3$ and with water, dried over sodium sulfate, and concentrated to dryness. The residue was taken up in the minimum amount of dichloromethane, precipitated at −70° C. by addition of hexane, and dried under vacuum; yield 100 mg; $^{31}$P NMR 146.02. The epiandrosterone-disulfide linked oligonucleotides were synthesized on Applied Biosystems automated gene synthesizer without final DMT removal. After completion, epiandrosterone-disulfide linked oligonucleotides were deprotected from the support under aqueous ammonia conditions and purified on HPLC using reverse phase column.

Reverse phase HPLC was performed with a Dionex DX500 system equipped with a Hewlett Packard ODS hypersil column (4.6×200 mm, 5 mm particle size) using 0.03 M $Et_3NH^+OAc^-$ buffer (TEAA), pH 7, with a 1%/min. gradient of 95% $CH_3CN$/5% TEAA. The flow rate was 1 mL/min. with UV detection at 260 nm. Preparative HPLC was used to purify the DMT-protected unmodified oligonucleotides. After collection and evaporation of the buffer, the DMT was cleaved from the oligonucleotides by treatment with 80% acetic acid for 30 min at room temperature. The solution was then evaporated to near dryness, water was added, and the cleaved DMT was extracted from the aqueous oligonucleotide solution using ethyl acetate. The amount of oligonucleotide was determined by absorbance at 260 nm, and final purity assessed by reverse phase HPLC.

3'-amino containing DNA was synthesized by following standard protocol for DNA synthesis on DNA synthesizer. The 3' amine modified DNA was attached to the solid support through an immobilized succinyl linker. After synthesis, DNA was cleaved from the solid support using aqueous ammonia, resulting in the generation of a DNA molecule containing a free amine at the 3'-end. The crude material was purified on HPLC as described above, using triethyl ammonium (TEA) buffer. 5' amino modified oligonucleotide was synthesized using standard protocols by incorporating 5' MMT protected amine modified phospharamidite which is commercially available from GLEN research.

Attachment of amino linked DNA to the isocyanate functionalized glass surface is preferably performed in presence of N,N'-dimethylformamide (DMF). Typically, 12 μM amine modified DNA was loaded on the glass surface and kept in the chamber for 12 h, then the glass plates are washed with water and ethanol and dried in the dessicator. After drying, these plates are ready for testing with DNA samples.

(c) Attachment of Oligonucleotides to Gold Nanoparticles

A colloidal solution of citrate stabilized gold nanoparticles (about 10 nM), prepared as described in part A above, was mixed with sulfur modified-$a_{20}$-probe oligonucleotide and corresponding sulfur modified-$da_{20}$ filler oligonucleotide (each to a concentration of 1.7 μM), prepared as described in part B, and allowed to stand for 24 hours at room temperature in 1 ml Eppendorf capped vials. Then, 100 μL of a 0.1 M sodium hydrogen phosphate buffer, pH 7.0, and 100 μL of 1.0 M NaCl were premixed and added to the solution and allowed to stand for an additional 40 hours. The solution was next centrifuged at 14,000 rpm in an Eppendorf Centrifuge 5414 for about 15 minutes to give a very pale pink supernatant containing most of the oligonucleotide (as indicated by the absorbance at 260 nm) along with 7-10% of the colloidal gold (as indicated by the absorbance at 520 nm), and a compact, dark, gelatinous residue at the bottom of the tube. The supernatant was removed, and the residue was resuspended in the desired aqueous buffer. In this Example, the buffer used includes 0.1 M NaCl, 10 mM phosphate, 0.01% sodium azide at pH 7.

The following nanoparticle-oligonucleotide conjugates specific for M-13 phage DNA were prepared in this manner:

Probe P1: $(a_{20})_m$-5'-S'-gold-S'-5'-$[a_{20}$-cgctcacaatt-3']$_n$ (SEQ ID NO: 1)

Probe P2: $(a_{20})_m$-5'-S'-gold-S'-5'-$[a_{20}$-tgaaattgttatc-3']$_n$ (SEQ ID NO:2)

S' indicates a connecting unit prepared via an epiandrosterone disulfide group; m and n are approximately the same since equal concentrations of the oligonucleotides were used in preparing the nanoparticle-oligonucleotide conjugates.

(d) M-13 Target Detection:

For M13 target detection, a stock solution containing target was prepared as follows:

1 μl of 100 nM 51mer synthetic DNA

2 μl of 1:2000 diluted Tween

2 μl of PCR buffer*

2 μl of probe P1 and P2 mix

1 μl 1:10 diluted salmon sperm DNA (Gibco BRL cat. No. 15632-011)

2 μl of 4 M NaCl buffer

10 μl of total mixture

* PCR buffer for amplification purchased from Applied Biosystems, Cat. No. N808-0249 (AmpliTaq Gold DNA polymerase kit).

A 27mer oligonucleotide having a poly A linker (SEQ ID NO: 3) was prepared with a 3'-terminal amino group as described above. This 27mer was used as capture probe for the target M-13 sequence. The 27mer oligonucleotide was attached to an isocyanate plate using the procedures described in Example 1. The target M-13 sequence to be detected is shown as SEQ ID NO:4.

Capture probe sequence: 5'-cca cac aac ata cga gcc gga agc ata-$a_{10}$-$NH_2$-3' [SEQ ID NO:3]

M-13 Target sequence: 5'-tat gct tcc ggc tcg tat gtt gtg tgg aat tgt gag cgg ata aca att tca-3' [SEQ ID NO:4]

A 1 ul aliquot of the stock solution was spotted on the DNA modified glass plate. A control solution (no DNA target) also prepared in the same fashion and 1 ul aliquot of the control solution was spotted on the same chip. The loaded glass plates were stored in a closed container under humid conditions for 2 h and was then washed with washing buffer (750 mM NaCl, 75 mM sodium citrate, 0.05% Tween at pH 7) and with 0.5 M $NaNO_3$ buffer at 23° C. The spots were then amplified with silver stain for 5 min and washed with nanopure water. The silver stain solutions A and B were purchased from Sigma Company, St. Louis, Mo. (catalog NoS-5020 (solution A) and S-5145 (solution B) and used according to the instructions therein. Both solutions are also available from Sigma Co. as a silver amplification kit. After signal amplification, the glass plates were scanned using a Hewlett Packard scan jet 5300C.

Figure 3:
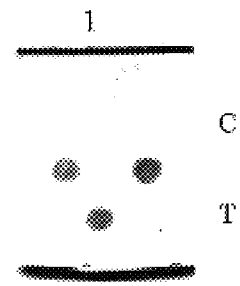
FIG. 3 illustrates M13 synthetic target detection and reproducibility using gold nanoparticle detection probes and capture probes bound to a glass surface prepared in accordance with the invention. See Example 2.
Figure 4:
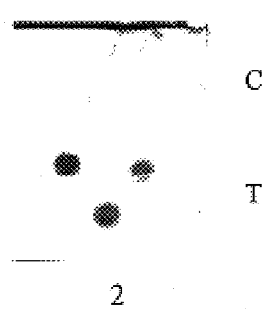
FIG. 4 is essentially the same as FIG. 3 and shows that target detection using plates prepared in accordance with the present invention is reproducible. See Example 2.

The results are shown in FIGS. 3 and 4. As shown in FIG. 3, no silver stain spots were observed for the controls and three silver stain spots were observed on the glass chip for areas spotted with the M-13 target solution as expected. In FIG. 4, same experiment was repeated to show the reproducibility of the target hybridization using complementary DNA capture probes immobilized onto isocyanate modified plates.

Example 3

Detection of MTHFR Sequence

This Example illustrates the use of oligonucleotides immobilized onto the isocyanate plates and its use for detecting a MTHFR target DNA sequence (SEQ ID NO:5). A capture probe having 3'-amino group and a PEG spacer were prepared as described below and were attached to an isocyanate immobilized glass surface in accordance with the procedure in Example 1.

MTHFR (wild type) PCR product sequence:

(SEQ ID NO:5)
5'ccttgaacaggtggaggccagcctctcctgactgtcatccctattggc aggttacccaaaggccaccccgaagcagggagctttgaggctgacctga agcacttgaaggagaaggtgtctgcgggagccgatttcatcatcacgcag cttttctttgaggctgacacattcttccgctttgtgaaggcatgcaccga catgggcatcacttgccccatcgtccccgggatctttcccatccaggtga ggggcccaggagagcccataagctccctccacccactctcaccgc-3'

MTHFR (mutant) PCR product sequence:

(SEQ ID NO:6)
5'ccttgaacaggtggaggccagcctctcctgactgtcatccctattggc aggttacccaaaggccaccccgaagcagggagctttgaggctgacctga agcacttgaaggagaaggtgtctgcgggagtcgatttcatcatcacgcag cttttctttgaggctgacacattcttccgctttgtgaaggcatgcaccga catgggcatcacttgccccatcgtccccgggatctttcccatccaggtga ggggcccaggagagcccataagctccctccacccactctcaccgc-3'

The following nanoparticle-oligonucleotide conjugates specific for MTHFR sequence were prepared as described in Example 2:
Probe P3: $(a_{20})_m$-5'-S'-gold-S'-5'-[$a_{20}$-cctcaaagaaaagc-3']$_n$ (SEQ ID NO: 7)
Probe P4: $(a_{20})_m$S-gold-S'-[5'$a_{20}$gcggaagaatgtgtc-3']$_n$ (SEQ ID NO:8)

S' indicates a connecting unit prepared via an epiandrosterone disulfide group; m and n are approximately the same since equal concentrations of the oligonucleotides were used in preparing the nanoparticle-oligonucleotide conjugates. The probes were stored in buffer as described in Example 2 prior to use.

A capture probe (3'-NH$_2$-PEG-cct cgg cta aag tag t-5') (SEQ ID NO:9) was prepared where PEG represents polyethylene glycol linker. The oligonucleotide synthesis was started with an 3'-amino support which is commercially available from Glen Research (Sterling, Va., USA; catalog No. 10-1918-90) on an automated synthesizer (Applied Biosystems, Inc., Foster City, Calif., USA; ; model Expedite). PEG linkers were incorporated from 3' end as a spacer (between the surface and oligonucleotide) into the oligonucleotide synthesis. Commercially available peg phosphoramidite was used for the automated synthesis and available from Glen Research. After incorporating peg linkers into the oligonucleotide synthesis, DNA synthesis was extended from 3' end. After completion oligonucletides were deprotected from the solid support and purified as described in Example 2.

Figure 5:
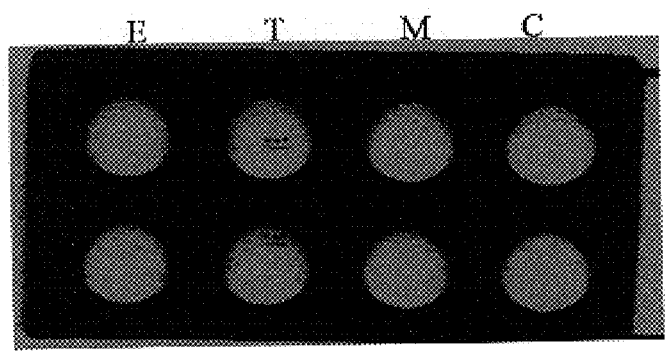
FIGS. 5 illustrates MTHFR 208 base pair target (mutant and wild type) SNP detection using gold nanoparticle detection probes and capture probes bound to a glass surface prepared in accordance with the invention. See Example 3.
Figure 6:
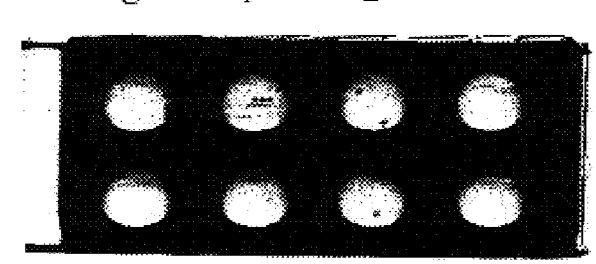
FIG. 6 is essentially the same as FIG. 5 and shows that target detection using plates prepared in accordance with the present invention is reproducible. See Example 3.

Experimental Procedure: To each well, mixture of 30 ml of the hybridization buffer (150 ul of SSC (3M NaCl, 0.3 M sodium citrate at pH 7), 90 ul of water, 60 ul of 0.5% Tween 20 detergent), 10 ml of colloid mix (probe P3 5 ml+ probe P4 5 ml), 10 ul of 208 base pair PCR amplified product (5-10 nM in PCR buffer (PCR buffer for amplification purchased from Applied Biosystems, Cat. No. N808-0249 (AmpliTaq Gold DNA polymerase kit) was added. After heating for 3 minutes, aliquots were cooled to room temperature and loaded on the plate and kept in the humidified chamber for 40 min at 40° C. After 40 minutes, the hybridization plates were washed with washing buffer (750 mM NaCl, 75 mM sodium citrate, 0.05% Tween at pH 7) and with 0.5M NaNO$_3$ buffer at 40° C. and amplified with silver A and B from Sigma. Same experiment was conducted on two different plates and the results, after silver amplification, are shown in FIG. 5 and FIG. 6. On both the plates, wild type and mutant targets were used to show SNIP differentiation.

Example 4

Positive Control Hybridization

In this Example, a nanoparticle-oligonucleotide probe was targeted directly to the capture strand (SEQ ID NO:10) bound to the glass plate using the isocyanate plates described in Example 1. Hence, the oligonucleotides bound to the nanoparticles has a sequence (SEQ ID NO:11) that is complementary to a portion of the capture oligonucleotides immobilized on the glass surface.

Capture strand sequence:
3'-ACT GGA CTG GAC TGG-5' (SEQ ID NO:10)
The following nanoparticle-oligonucleotide conjugate probe specific for capture oligonucleotide were prepared as described in Example 2:
Probe P9: $(a_{20})_m$-5'-S'-gold-S'-5'-[$a_{20}$-tgacctgacctgacc-3']$_n$ (SEQ ID NO: 11)

S' indicates a connecting unit prepared via an epiandrosterone disulfide group; m and n are approximately the same since equal concentrations of the oligonucleotides were used in preparing the nanoparticle-oligonucleotide conjugates.

Figure 7:
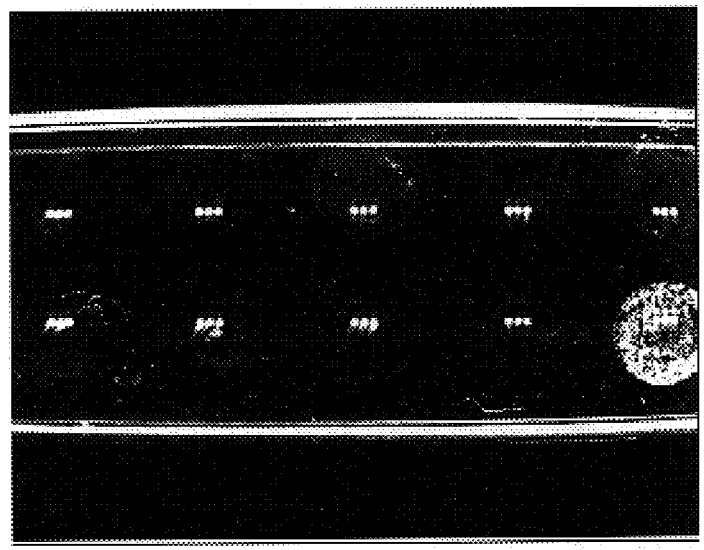
FIG. 7 illustrates the targeting of a nanoparticle probe directly to the capture DNA bound to a glass surface prepared in accordance with the invention. See Example 4.

Procedure: A hybridization buffer was prepared and included 150 ul of SSC (3M NaCl, 0.3 M sodium citrate at pH 7), 90 ul of water, 60 ul of 0.5% Tween 20 detergent. To each well in the capture probe immobilized plate prepared as described in Example 2, a mixture of 25 ul of hybridization buffer, 25 ul of water, 5 ul of 10 nM gold colloid probe P9 was added and hybridized at 52° C. for 45 minutes. After washing thoroughly with washing buffer (750 mM NaCl, 75 mM sodium citrate, 0.05% Tween at pH 7) and with 0.5M NaNO$_3$ buffer at 23° C., plates were amplified with Sigma silver solution A and B. After signal amplification, the glass plates were scanned using a Hewlett Packard scan jet 5300C. From this experiment (see FIG. 7), it was concluded that gold nanoparticles probes hybridized directly to the capture strands under the hybridization conditions.

Example 5

Detection of Factor V Target Sequence

In this Example, a Factor V sequence sandwich hybridization assay was performed using a Factor V 99 base pair PCR amplified product of defined sequence (SEQ ID NO:12). In addition, a DNA capture probe (SEQ ID NO:13) including a PEG (polyethylene glycol) linker was prepared using the procedure described in Examples 2 and 3. This capture probe was immobilized onto isocyanate-linked plates and free amines were subsequently capped as described in Example 1.

Factor V 99base PCR pair product sequence:

(SEQ ID NO:12)
5'gacatcgcctctgggctaataggactacttctaatctgtaagagcaga
tccctggacaggcaaggaatacaggtattttgtccttgaagtaacctttc
ag 3'

Capture strand sequence:
5'-ctg ctc tta cag att aga agt agt cct-PEG-PEG-PEG-NH$_2$-3' (SEQ ID NO:13)

The following nanoparticle-oligonucleotide conjugates specific for the synthetic target sequence were prepared in accordance with the procedure outlined in Example 2:

Probe 13D: $(a_{20})_m$-5'-S'-gold-S'-5'-[$a_{20}$-tattcctcgcc-3']$_n$ (SEQ ID NO: 14)

Probe 26D: $(a_{20})_m$-5'-S'-gold-S'-5'-[$a_{20}$-attccttgcct-3']$_n$ (SEQ ID NO:15)

S' indicates a connecting unit prepared via an epiandrosterone disulfide group; m and n are approximately the same since equal concentrations of the oligonucleotides were used in preparing the nanoparticle-oligonucleotide conjugates. The probes were stored in buffer as described in Example 2 prior to use.

Figure 8:
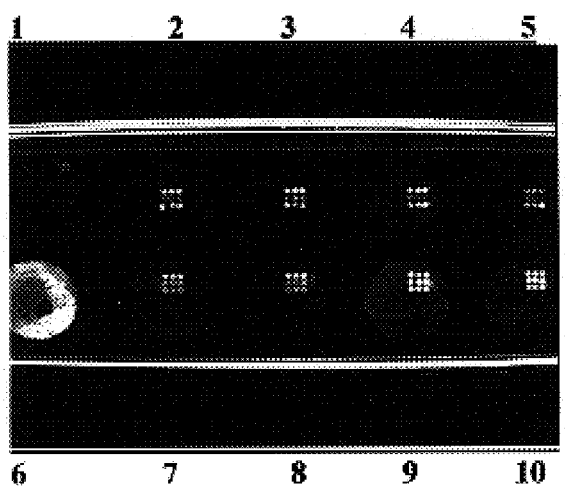
FIG. 8 illustrates Factor V 99 base pair PCR product target detection using gold nanoparticle detection probes and capture probes bound to a glass surface prepared in accordance with the invention. See Example 5.

Experimental Procedure: A hybridization buffer was prepared as follows: 150 ul of SSC (3M NaCl, 0.3 M sodium citrate at pH 7), 90 ul of water, 60 ul of 0.5% Tween 20 detergent. To each well, a mixture of 30 ul of the hybridization buffer, 10 ul of either probes 13D or 26D and 10 ul of PCR product (5-10 nM in PCR buffer (PCR buffer for amplification purchased from Applied Biosystems, Cat. No. N808-0249 (AmpliTaq Gold DNA polymerase kit)) was added. After loading the aliquots, the plates were kept in the humidified chamber for 2 h at room temperature. After 2 h, the hybridization plates washed with washing buffer (750 mM NaCl, 75 mM sodium citrate, 0.05% Tween at pH 7) and with 0.5M NaNO$_3$ buffer at 23° C. and amplified with silver A and B from Sigma. Wells 1 and 6 were used as controls (no DNA target was added) to the hybridization aliquots and water was added in place of target stock solution. After signal amplification, the glass plates were scanned using a Hewlett Packard scan jet 5300C. As expected, wells 1 and 6 did not show any spots and rest of the wells showed the target presence spots (FIG. 8).

Example 6

Detection of MTHFR Target Sequence

This Example is the same as the one described in Example 3 except three different MTHFR target sequences of various sizes were used and were labeled as PCR products 75 (SEQ ID NO:16), 119 (SEQ ID NO:17), 208 (SEQ ID NO:18), and. The purpose of this experiment was to evaluate the effect of different sized targets on hybridization. A 3-amino DNA capture probe (SEQ ID NO:19) having a PEG spacer was prepared as described in Example 3 and was used for immobilization onto isocyanate plates in accordance with Example 1. Nanoparticle-oligonucleotide detection probes 65D (SEQ ID NO:20) and 66D (SEQ ID NO:21) were prepared as described in Example 2.

75 base pair PCR product:

(SEQ ID NO:16)
5'gaggctgacctgaagcacttgaaggagaaggtgtctgcgggagccgat
              ttcatcatcacgcagcttttctttgag-3'

119 base pair PCR product:

(SEQ ID NO:17)
5'tattggcaggttaccccaaaggccaccccgaagcagggagctttgagg
ctgacctgaagcacttgaaggagaaggtgtctgcgggagccgatttcatc
atcacgcagcttttctttgag-3'

208 base pair PCR product:

(SEQ ID NO:18)
5'ccttgaacaggtggaggccagcctctcctgactgtcatccctattggc aggttaccccaaaggccaccccgaagcagggagctttgaggctgacctga agcacttgaaggagaaggtgtctgcgggagccgatttcatcatcacgcag cttttctttgaggctgacacattcttccgctttgtgaaggcatgcaccga catgggcatcacttgccccatcgtccccgggatcttcccatccaggtga ggggcccaggagagcccataagctccctccaccccactctcaccgc Capture probe sequence:
3'-NH$_2$-PEG-tcc aca gac gcc ctc ggc ta-5' (SEQ ID NO:19)

The following nanoparticle-oligonucleotide conjugates specific for the synthetic target sequence were prepared in accordance with the procedure outlined in Example 2:

Probe 65D: $(a_{20})_m$-5'-S'-gold-S'-5'-[$a_{20}$-gcgtgatgatgaaa-3']$_n$ (SEQ ID NO: 20)

Probe 66D: $(a_{20})_m$-5'-S'-gold-S'-5'-[$a_{20}$-cctcaaagaaaag-3']$_n$ (SEQ ID NO:21)

where S' indicates a connecting unit prepared via an epiandrosterone disulfide group; m and n are approximately the same since equal concentrations of the oligonucleotides were used in preparing the nanoparticle-oligonucleotide conjugates.

Figure 9:
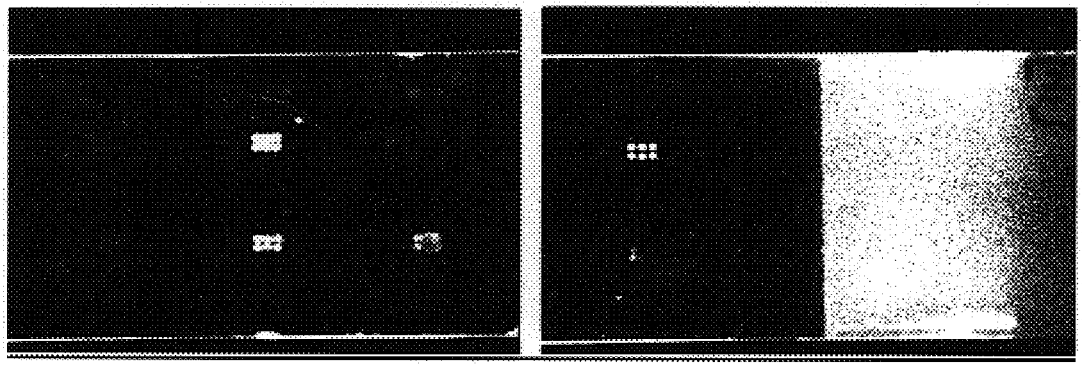
FIG. 9 illustrates detection of different target lengths of MTHFR PCR products (208, 119 and 75 base pairs) detection on the same plate using gold nanoparticle detection probes and capture probes bound to a glass surface prepared in accordance with the invention. See Example 6.
Figure 10:
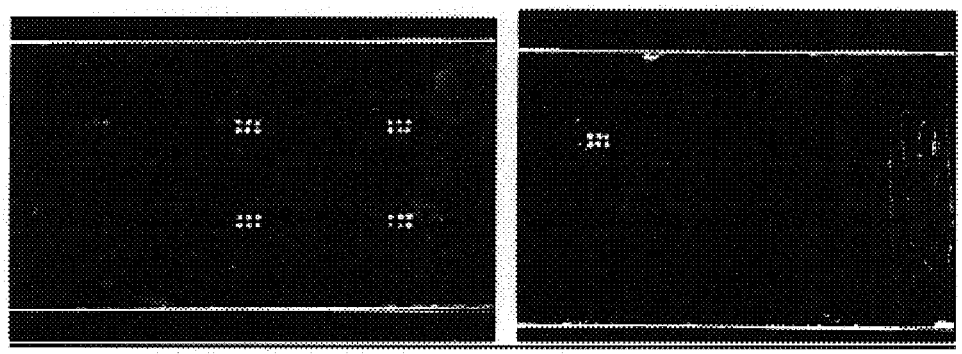
FIG. 10 is essentially the same as FIG. 9 and shows that target detection using plates prepared in accordance with the present invention is reproducible. See Example 6.

Experimental Procedure: A hybridization buffer was prepared and included the following components: 150 ul of SSC (3M NaCl, 0.3 M sodium citrate at pH 7), 90 ul of water, 60 ul of 0.5% Tween 20 detergent. To each well, mixture of 30 ul of the hybridization buffer, 10 ul of probe mix (65D 5 ul, 66D 5 ul), 10 ul of PCR product (5-10 nM in PCR buffer (PCR buffer for amplification purchased from Applied Biosystems, Cat. No. N808-0249 (AmpliTaq Gold DNA polymerase kit)) was added. The 50 ul Aliquots were loaded on the plates and the plates where then kept in the humidified chamber for 40 minutes at 40° C. After the 40 minute hybridization reaction was completed, the plates were washed with washing buffer (750 mM NaCl, 75 mM sodium citrate, 0.05% Tween at pH 7) and with 0.5M NaNO$_3$ buffer at 35° C. and amplified with silver A and B from Sigma. The same experiment was conducted on two glass plates with different thicknesses to see if there are any differences in spot morphology. After signal amplification, the glass plates were scanned using a Hewlett Packard scan jet 5300C. In FIG. 9, the plate thickness was 1.2 mm while in FIG. 10, the plate thickness was 1.0 mm The Figures show that detection of different target lengths is possible. Moreover, no conclusive difference in spot morphology was seen Example 7

Detection of MTHFR Wild-Type and Mutant Sequences

This Example illustrates detection of MTHFR wild-type and mutant sequences. Two PCR amplified wild type (SEQ ID NO:22) and mutant MTHFR (SEQ ID NO:23) sequences were synthesized and used as target sequences for this Example. The 3' amino DNA capture probe sequence (SEQ ID NO:24) including a PEG spacer was prepared as described in Example 3. The capture probe was immobilized onto isocyanate glass plates as described in Example 1. Two gold nanoparticle-oligonucleotide conjugate detection probes 13D' (SEQ ID NO:25) and 14D' (SEQ ID NO:26) were prepared as described in Example 2.

75 base pair (Wild-Type) product target sequence:

(SEQ ID NO:22)
5'gaggctgacctgaagcacttgaaggagaaggtgtctgcgggagccgat
ttcatcatcacgcagcttttctttgag-3'

75 (mutant) base pair (mutant) product target sequence:

(SEQ ID NO:23)
5'gaggctgacctgaagcacttgaaggagaaggtgtctgcgggagtcgat
ttcatcatcacgcagcttttctttgag-3'

Capture probe sequence:
5'-ccc gca gac acc ttc tcc ttc-PEG-$NH_2$-3' (SEQ ID NO:24)

The following nanoparticle-oligonucleotide conjugates specific for the synthetic target sequence were prepared in accordance with the procedure outlined in Example 2:

Probe 13D': $(a_{20})_m$-5'-S'-gold-S'-5'-$[a_{20}$-tgatgaaatcgact-3'$]_n$ (SEQ ID NO:25)

Probe 14D': $(a_{20})_m$-5'-S'-gold-S'-5'-$[a_{20}$-atgaaatcggct-3'$]_n$ (SEQ ID NO:26)

S' indicates a connecting unit prepared via an epiandrosterone disulfide; m and n are approximately the same since equal concentrations of the oligonucleotides were used in preparing the nanoparticle-oligonucleotide conjugates. The probes were stored in buffer as described in Example 2 prior to use.

Figure 11:
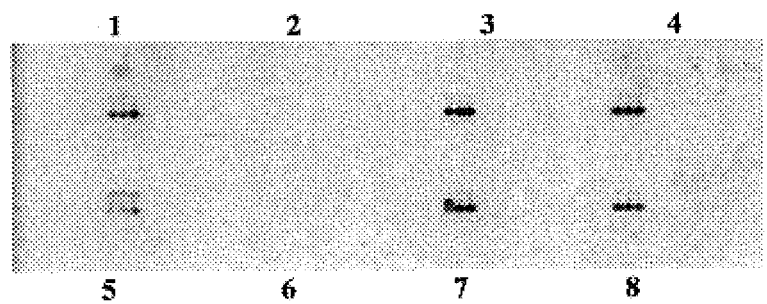
FIG. 11 illustrates MTHFR 75 base pair detection using gold nanoparticle detection probes and capture probes bound to a glass surface prepared in accordance with the invention. See Example 7.

Experimental Procedure: A hybridization buffer was prepared and included the following components: 150 ul of SSC (3M NaCl, 0.3 M sodium citrate at pH 7), 90 ul of water, 60 ul of 0.5% Tween 20 detergent. To each well, a mixture of 30 ul of the hybridization buffer, 10 ul of probe 13D' or 14D', and 10 ul of PCR target product (5-10 nM in PCR buffer (PCR buffer for amplification purchased from Applied Biosystems, Cat. No. N808-0249 (AmpliTaq Gold DNA polymerase kit) was added. Aliquots were loaded on the plate and the plate was kept in the humidified chamber for 2 h at room temperature. After completion of the 2 h hybridization reaction, the plates were washed with washing buffer (750 mM NaCl, 75 mM sodium citrate, 0.05% Tween at pH 7) and with 0.5 M $NaNO_3$ buffer at 35° C. and amplified with silver A and B from Sigma. After amplification, the glass slide was scanned under Hewlett Packard scan jet 5300C (FIG. 11). As expected, the controls did not show up as spots on the slide. Both wild type and mutant targets were showed up as dark spots since plates were washed at lower stringency that is 35° C.

Wells were loaded on the plate in the following order:
Well 1---14D' probe with 75mer mutant target
Well 2---13D' probe without any target (control)
Well 3---13D' probe with 75mer wild type target
Well 4---13D' probe with 75mer mutant type target
Well 5---13D' probe with 75mer mutant type target
Well 6---14D' probe without any target (control)
Well 7---13D' probe with 75mer wild type target
Well 8---14D' probe with 75mer mutant type target Example 8

2-Deoxy Glucosaminic Acid (Carbohydrate) Addition to Isocyanate Plate and Coupling with Capture DNA and Target Detection This Example describes attachment of a carbohydrate linker to an isocyanate plate and attachment of a nucleic acid molecule to the linker and the use of the nucleic acid modified plate for detection of a target nucleic acid molecule. FIG. 12 is a schematic diagram illustrating the stepwise modification of the glass plate. As shown in FIG. 12, amino-group containing sugar molecules contained in an water/organic solvent mixture solution were reacted with the isocyanate linked glass surface to immobilize the sugar molecule onto the plate. Thereafter, a second molecule including a functional group (an amino-group containing DNA capture probe) is coupled to the first molecule immobilized onto the surface in the presence of a coupling agent such as EDC.

(a) Glass Slide Fictionalization and Attachment of Capture Strand to Modified Glass Surface:

Pre-cleaned glass slides were functionalized with silyl-isocyanate as described in Example 1. The highly reactive isocyanate sites were treated with 2'-deoxy glucosaminic acid (4 gm in 100 ml of water) in aqueous solution for one hour at room temperature. Thereafter, the immobilized plates were washed with water and ethanol successively and dried. The carboxylic acid moiety of the carbohydrate molecule was coupled with 3'-amino DNA capture probe (SEQ ID NO:28) using standard carbodiimide coupling conditions. The capture probe having a free 3' amine was synthesized on Expedite (PE Bio systems) DNA synthesizer in accordance with Example 2. After synthesis, aqueous ammonia was used to release the DNA from the solid support, resulting in the generation of DNA strand containing a free amine group at the 3'-end. The crude DNA strand obtained was purified on C 18 column (Agilent), reverse phase HPLC as described in Example 2.

Attachment of the 3'-$NH_2$ modified DNA to the carbohydrate linked glass surface was accomplished by adding 1-ethyl-3-(-3-dimethylaminopropyl) carbodiimide hydrochloride (EDC) and N-hydroxysulfosuccinimide (sulfo-NHS) to a 20 µM solution of the capture probe in activation buffer, 100 mM 2-N-morpholinoethanesulfonic acid (MES) at pH 6. The solution was incubated at room temperature for 15 minutes and then 10 ul aliquots were spotted on the glass surface. Only a portion of the glass plate was functionalized with capture oligonucleotides. These areas were subsequently spotted with the target DNA solution.

(b) Detection of Target Nucleic Acids:

A synthetic target sequence (SEQ ID NO:27) as well as capture probe oligonucleotides (SEQ ID NO:28) and gold nanoparticle-oligonucleotide detection probes having sequences complementary to the synthetic target sequences were prepared as described in Example 2.

Target sequence:

(SEQ ID NO:27)
5'aagcacttgaaggagaaggtgtctgcgggagccgatttcatcatcacg
cagcttttctttgaggctgacacattcttccgctttgtgaaggcatgcac
cg 3'

Capture probe sequence:
3'-NH$_2$-tcc aca gacgcc ctc ggc t-5 (SEQ ID NO:28)

The following nanoparticle-oligonucleotide conjugates specific for the synthetic target sequence were prepared in accordance with the procedure outlined in Example 2:

Probe P5: (a$_{20}$)$_m$-5'-S'-gold-S'-5'-[a$_{20}$-cctcaaagaaaagc-3']$_n$ (SEQ ID NO:29)

Probe P6: (a$_{20}$)$_m$-5'-S'-gold-S'5'-[a$_{20}$-aaagcggaagaatgtgtc-3']$_n$ (SEQ ID NO :30)

S' indicates a connecting unit prepared via an epiandrosterone disulfide group; m and n are approximately the same since equal concentrations of the oligonucleotides were used in preparing the nanoparticle-oligonucleotide conjugates. Stock solutions of nanoparticle probes P5 and P6 were prepared as described in Example 2.

Oligonucleotide capture probe immobilized glass plates were prepared via 2'-deoxy glucosaminic acid linker as described above.

A stock target solution was prepared as follows:

Protocol:
2 µl of the target. sequence
2 µl of the 1:10 diluted salmon sperm DNA (Gibco BRL cat. No. 15632-011)
2 µl of 0.05% Tween 20.
2 µl of the Hybridization buffer
2 µl of the probes P5 and P6
10 µl Total (b) Hybridization: Hybridization buffer (0.75 M NaCl, 7.5 mM MgCl$_2$, 7.5 mM NaPO$_4$, pH 7, 0.005% SDS), 2 µl of salmon DNA (1:10 diluted from neat commercial sample), 2 µl of 0.05% Tween 20, 1 ul of DNA target (1 µM in 10 mM phosphate buffer, pH 7) and 2 nM gold nanoparticle probes were mixed in an eppendorf tube. The mixture was incubated for 10 minutes and spotted 1 µl on the glass chip area that was exactly modified with DNA capture probe. The glass chip was kept in humidified chamber for 1 h at room temperature. After hybridization, the plate was washed with washing buffer (750 mM NaCl, 75 mM sodium citrate, 0.05% Tween at pH 7) and with 0.5M NaNO$_3$ buffer at 23° C., and air dried.

(c) Silver staining detection: After hybridization and for detection purposes, equal amounts of silver solution A and B (SIGMA) were mixed and applied on the glass surface such that the surface was fully covered with silver solution. After 5 minutes, the glass chip was washed with water. The silver stain procedure was repeated to improve the intensity of the silver spots. After signal amplification, the glass plates were scanned using a Hewlett Packard scan jet 5300C. FIG. 13 demonstrates the detection of MTHFR synthetic target sequence clearly. Four controls and four target spots were maintained on the glass chip.

Example 9

Glycine (Amino Acid) Addition to Isocyanate Plates and Coupling with Capture DNA and Target Detection This Example describes attachment of a carbohydrate linker to an isocyanate plate and subsequent attachment of a nucleic acid molecule to the linker and the use of the nucleic acid modified plate for detection of a target nucleic acid molecule. FIG. 14 illustrates a schematic diagram for the stepwise attachment of a DNA capture probe via amino acid linker to an isocyanate modified glass plate. As shown in FIG. 14, amino acid molecules in aqueous solution were reacted with the isocyanate linked glass surface to immobilize the amino acid onto the plate. Thereafter, a second molecule including a functional group (an amino-group containing DNA capture probe) is coupled to the first molecule immobilized onto the surface in the presence of a coupling agent such as EDAC.

(a) Glass Slide Functionalization and Attachment of Capture Strand to Modified Glass Surface:

Pre-cleaned glass slides were functionalized with silyl-isocyanate as described in Example 1. The highly reactive isocyanate sites were treated with glycine (1 gm in 100 ml of water) in aqueous solution for one hour at room temperature. Thereafter, the plates were washed with water and ethanol successively and dried. The carboxylic acid site of the amino acid part was coupled with 3'-NH$_2$-tcc aca gacgcc ctc ggc t-5' DNA capture probe (SEQ ID NO: 14) using standard carbodiimide coupling conditions. The capture oligomer was synthesized on Expedite (PE Bio systems) DNA synthesizer in accordance with Example 2. After synthesis, aqueous ammonia was used to release the DNA from the solid support, resulting in the generation of DNA strand containing a free amine group at the 3'-end. The crude DNA strand obtained was purified on C 18 column (Agilent), reverse phase HPLC as discussed in Example 2.

The same methodology used to prepare the carbohydrate linked plates in Example 4 was used here also to detect the same target DNA. In addition, the same capture probes and gold nanoparticle probes described in Example 4 were used to detect the target DNA. All conditions were the same as described in Example 4 except a different linker (amino acid instead of carbohydrate) was used here. After signal amplification, the glass plates were scanned using a Hewlett Packard scan jet 5300C. The results are shown in FIG. 15. FIG. 15 shows that no silver spots were observed for the three controls. A silver spot was observed for the one target as expected.

In conclusion, it has been demonstrated that detection of different target DNA sequences are possible using capture probes immobilized onto the isocyanate modified glass plates. While DNA modified gold nanoparticle probes were used for detection, any suitable detection labels besides gold nanoparticles may be used such as chromophores, radiolabels, fluorescent labels, and Raman labels. Using this inventive method, amino group linked oligonucleotides, carbohydrates, amino acids; peptides and amino group linked small molecules can immobilize on glass surface in a simple way for detection. In the same fashion, hydroxyl group containing molecules may also be reacted on the isocyanate modified surface and detected with different reporter molecules, however, the reaction rate is slow relative to amino group containing molecules.

REFERENCES

1. *Nucleic Acids research*, vol 22, 5456-5465 (1994).
   Direct fluorescence analysis of genetic polymorphism by hybridization with oligonucleotide arrays on glass supports.
2. *Nucleic Acids research*, vol 24, 3040-3047 (1996).
   Fabrication of patterned DNA surfaces.
3. *Nucleic Acids research*, vol 24,3031-3039(1996).
   Covalent attachment of synthetic DNA to self-assembled monolayer films.

4. *Nucleic Acids research*, vol 27, 1970-1977 (1999).
   Versatile derivatisation of solid support media for covalent bonding on DNA-microchips.
5. *Angew .Chem. Int. Ed*, 38, No.9, 1297(1999)
   Covalent surface functionalization and self-organization of silica nanoparticles.
6. *Analytical biochemistry* 280, 143-150 (2000).
   Comparison between different strategies of covalent attachment of DNA to glass surfaces to build DNA microarrays.
7. *Nucleic Acids research*, vol 29, 955-959 (2001).
   Immobilization of oligodeoxyribonucleotides with multiple anchors to microchips.

What is claimed:

1. A method for immobilizing a probe on a glass surface comprising the steps of:
   (a) reacting the glass surface with a solution at room temperature to provide immobilized reactive moieties, the solution comprising (3-isocyanatopropyl) triethoxysilane, an organic solvent, and an acid; and
   (b) reacting the immobilized reactive moieties with an amino-group containing molecule so as to immobilize said molecule on the glass surface, wherein the amino-group containing molecule further comprises one or more functional groups;
   (c) reacting the immobilized amino-group containing molecule on the surface with 1-(3-dimethylaminopropyl)-3-ethylcarbodiimide hydrochloride (EDC) that reacts with a functional group of the immobilized amino-group containing molecule so as to produce second immobilized reactive moieties; and
   (d) reacting the second immobilized reactive moieties with a second molecule having a functional group capable of reacting with the second immobilized reactive moieties.

2. The method of claim 1 wherein the second molecule is a probe.

3. The method of claim 2, wherein the probe is selected from the group consisting of a protein, a peptide, a nucleic acid, a peptide nucleic acid, a linked nucleic acid, an amino acid, a nucleoside triphosphate, a carbohydrate, a lipid, a lipid bound protein, an aptamer, a virus, a cell fragment, and a whole cell.

4. The method of claim 2, wherein the probe has been derivatized to contain one or more amino and/or hydroxyl groups.

5. The method of claim 4, wherein the probe has been derivatized to contain one or more amino groups.

6. The method according to claim 1 wherein the (3-isocyanatopropyl) triethoxysilane is present in solution at a concentration ranging between about 20 mM and about 200 mM.

7. The method of claim 1 wherein the amino-group containing molecule immobilized on the surface has at least one carboxyl group.

8. The method of claim 7 wherein the second molecule has at least one amino group.

9. The method of claim 7 wherein the second immobilized reactive moieties are the reaction products of the carboxyl group with 1-(3-dimethylaminopropyl)-3-ethylcarbodiimide hydrochloride (EDC).

10. The method according to claim 1, wherein the amount of acid in the solution is between about 0.01 % (v/v) to about 0.1 % (v/v).

11. A method for immobilizing an amino-group containing molecule on a surface having free hydroxyl groups comprising the steps of:
   (a) reacting said surface with a solution at room temperature to provide immobilized reactive moieties, the solution comprising a silyl isocyanate derivatizing agent, an organic solvent, and an acid, the silyl isocyanate agent having a formula:

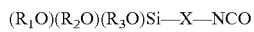
   (R$_1$O)(R$_2$O)(R$_3$O)Si—X—NCO wherein R$_1$R$_2$ and R$_3$ independently represents C$_1$-C$_6$ alkyl, phenyl, or aryl substituted with one or more groups selected from the group consisting of C$_1$-C$_6$ alkyl and C$_1$-C$_6$ alkoxy; X represents linear or branched C$_1$-C$_{20}$ alkyl or aryl substituted with one or more groups selected from the group consisting of C$_1$C$_6$ alkyl and C$_1$-C$_6$ alkoxy, optionally substituted with one or more heteroatoms comrrising oxygen, nitrogen, and sulfur;
   (b) reacting the immobilized reactive moieties with the amino-group containing molecule so as to immobilize the amino-group containing molecule on the surface, wherein the amino-group containing molecule further includes one or more functional groups and comprises a carboxyl group;
   (c) reacting the immobilized amino-group containing molecule on the surface with a chemical agent that reacts with a functional group of the amino-group containing molecule so as to produce second immobilized reactive moieties; and
   (d) reacting the second immobilized reactive moieties with a second molecule having a functional group capable of reacting with the second immobilized reactive moieties.

12. The method of claim 11, wherein the chemical agent is 1-(3-dimethylaminopropyl)-3-ethylcarbodiimide hydrochloride (EDC), and the second immobilized reactive moieties are the reaction products of the carboxyl group with EDC.

13. The method of claim 12, wherein the second molecule contains or has been derivatized to contain one or more amino groups.

* * * * *

```
                              SEQUENCE LISTING

<160> NUMBER OF SEQ ID NOS: 32

<210> SEQ ID NO 1
<211> LENGTH: 31
<212> TYPE: DNA
<213> ORGANISM: Artificial Sequence
<220> FEATURE:
<223> OTHER INFORMATION: oligonucleotide probe modified with gold
      nanoparticle
<220> FEATURE:
<221> NAME/KEY: misc_feature
<222> LOCATION: (1)..(1)
<223> OTHER INFORMATION: n is a deoxyadenosine residue modified in 5'
      with an epiandroster one disulfide-gold
      nanoparticle-epiandrosterone disulfide conjugate

<400> SEQUENCE: 1
naaaaaaaaa aaaaaaaaaa cgctcacaat t                                    31

<210> SEQ ID NO 2
<211> LENGTH: 33
<212> TYPE: DNA
<213> ORGANISM: Artificial Sequence
<220> FEATURE:
<223> OTHER INFORMATION: oligonucleotide probe modified with gold
      nanoparticle
<220> FEATURE:
<221> NAME/KEY: misc_feature
<222> LOCATION: (1)..(1)
<223> OTHER INFORMATION: n is a deoxyadenosine residue modified with an
      epiandrosterone disulfide-gold nanoparticle-epiandrosterone
      disulfide conjugate

<400> SEQUENCE: 2
naaaaaaaaa aaaaaaaaaa tgaaattgtt atc                                  33

<210> SEQ ID NO 3
<211> LENGTH: 37
<212> TYPE: DNA
<213> ORGANISM: Artificial Sequence
<220> FEATURE:
<223> OTHER INFORMATION: amine-modified oligonucleotide
<220> FEATURE:
<221> NAME/KEY: misc_feature
<222> LOCATION: (37)..(37)
<223> OTHER INFORMATION: n is 3' amino-substituted deoxyadenosine
      (4-Amino-2-(6-amino-purin-9-yl)-5-hydroxymethyl-tetrahydro-furan-
      3-ol)

<400> SEQUENCE: 3
ccacacaaca tacgagccgg aagcataaaa aaaaaan                              37

<210> SEQ ID NO 4
<211> LENGTH: 51
<212> TYPE: DNA
<213> ORGANISM: Bacteriophage M13mp18

<400> SEQUENCE: 4
tatgcttccg gctcgtatgt tgtgtggaat tgtgagcgga taacaatttc a              51
```

```
<210> SEQ ID NO 5
<211> LENGTH: 294
<212> TYPE: DNA
<213> ORGANISM: Homo sapiens

<400> SEQUENCE: 5
ccttgaacag gtggaggcca gcctctcctg actgtcatcc ctattggcag gttaccccaa      60
aggccacccc gaagcaggga gctttgaggc tgacctgaag cacttgaagg agaaggtgtc     120
tgcgggagcc gatttcatca tcacgcagct tttctttgag gctgacacat tcttccgctt     180
tgtgaaggca tgcaccgaca tgggcatcac ttgccccatc gtccccggga tctttcccat     240
ccaggtgagg ggcccaggag agcccataag ctccctccac cccactctca ccgc           294

<210> SEQ ID NO 6
<211> LENGTH: 294
<212> TYPE: DNA
<213> ORGANISM: Homo sapiens

<400> SEQUENCE: 6
ccttgaacag gtggaggcca gcctctcctg actgtcatcc ctattggcag gttaccccaa      60
aggccacccc gaagcaggga gctttgaggc tgacctgaag cacttgaagg agaaggtgtc     120
tgcgggagtc gatttcatca tcacgcagct tttctttgag gctgacacat tcttccgctt     180
tgtgaaggca tgcaccgaca tgggcatcac ttgccccatc gtccccggga tctttcccat     240
ccaggtgagg ggcccaggag agcccataag ctccctccac cccactctca ccgc           294

<210> SEQ ID NO 7
<211> LENGTH: 34
<212> TYPE: DNA
<213> ORGANISM: Artificial Sequence
<220> FEATURE:
<223> OTHER INFORMATION: oligonucleotide probe modified with gold
      nanoparticle
<220> FEATURE:
<221> NAME/KEY: misc_feature
<222> LOCATION: (1)..(1)
<223> OTHER INFORMATION: n is deoxyadenosine modified at the 5' end with
      an epiandrosterone disulfide - gold nanoparticle - epiandrosterone
      disulfide conjugate

<400> SEQUENCE: 7
naaaaaaaaa aaaaaaaaaa cctcaaagaa aagc                                  34

<210> SEQ ID NO 8
<211> LENGTH: 35
<212> TYPE: DNA
<213> ORGANISM: Artificial Sequence
<220> FEATURE:
<223> OTHER INFORMATION: oligonucleotide probe modified with gold
      nanoparticle
<220> FEATURE:
<221> NAME/KEY: misc_feature
<222> LOCATION: (1)..(1)
<223> OTHER INFORMATION: n is deoxyadenosine modified at the 5' end with
      an epiandrosterone disulfide - gold nanoparticle - epiandrosterone
      disulfide conjugate

<400> SEQUENCE: 8
naaaaaaaaa aaaaaaaaaa gcggaagaat gtgtc                                 35

<210> SEQ ID NO 9
<211> LENGTH: 17
<212> TYPE: DNA
```

```
<213> ORGANISM: Artificial Sequence
<220> FEATURE:
<223> OTHER INFORMATION: polyetyleneglycolamino-modified oligonucleotide
<220> FEATURE:
<221> NAME/KEY: misc_feature
<222> LOCATION: (17)..(17)
<223> OTHER INFORMATION: n is 3' polyethyleneglycolamine deoxycitosine

<400> SEQUENCE: 9
tgatgaaatc ggctccn                                                 17

<210> SEQ ID NO 10
<211> LENGTH: 15
<212> TYPE: DNA
<213> ORGANISM: Homo sapiens

<400> SEQUENCE: 10
ggtcaggtca ggtca                                                   15

<210> SEQ ID NO 11
<211> LENGTH: 35
<212> TYPE: DNA
<213> ORGANISM: Artificial Sequence
<220> FEATURE:
<223> OTHER INFORMATION: oligonucleotide probe modified with gold
      nanoparticle
<220> FEATURE:
<221> NAME/KEY: misc_feature
<222> LOCATION: (1)..(1)
<223> OTHER INFORMATION: n is a deoxyadenosine residue modified with an
      epiandrosterone disulfide-gold nanoparticle-epiandrosterone
      disulfide conjugate

<400> SEQUENCE: 11
naaaaaaaaa aaaaaaaaaa tgacctgacc tgacc                             35

<210> SEQ ID NO 12
<211> LENGTH: 100
<212> TYPE: DNA
<213> ORGANISM: Artificial Sequence
<220> FEATURE:
<223> OTHER INFORMATION: PCR amplimer

<400> SEQUENCE: 12
gacatcgcct ctgggctaat aggactactt ctaatctgta agagcagatc cctggacagg   60
caaggaatac aggtattttg tccttgaagt aacctttcag                        100

<210> SEQ ID NO 13
<211> LENGTH: 27
<212> TYPE: DNA
<213> ORGANISM: Artificial Sequence
<220> FEATURE:
<223> OTHER INFORMATION: tripolyethyleneglycolamino-modified
      oligonucleotide
<220> FEATURE:
<221> NAME/KEY: misc_feature
<222> LOCATION: (27)..(27)
<223> OTHER INFORMATION: n is deoxythymidine substituted in 3' with a
      tripolyethyleneglycolamino group

<400> SEQUENCE: 13
ctgctcttac agattagaag tagtccn                                      27

<210> SEQ ID NO 14
<211> LENGTH: 31
<212> TYPE: DNA
<213> ORGANISM: Artificial Sequence
<220> FEATURE:
```

```
<223> OTHER INFORMATION: oligonucleotide probe modified with gold
      nanoparticle
<220> FEATURE:
<221> NAME/KEY: misc_feature
<222> LOCATION: (1)..(1)
<223> OTHER INFORMATION: n is a deoxyadenosine residue modified in 5'
      with an epiandroster one disulfide-gold
      nanoparticle-epiandrosterone disulfide conjugate

<400> SEQUENCE: 14
naaaaaaaaa aaaaaaaaaa tattcctcgc c                                 31

<210> SEQ ID NO 15
<211> LENGTH: 31
<212> TYPE: DNA
<213> ORGANISM: Artificial Sequence
<220> FEATURE:
<223> OTHER INFORMATION: oligonucleotide probe modified with gold
      nanoparticle
<220> FEATURE:
<221> NAME/KEY: misc_feature
<222> LOCATION: (1)..(1)
<223> OTHER INFORMATION: n is a deoxyadenosine residue modified in 5'
      with an epiandrosterone disulfide-gold
      nanoparticle-epiandrosterone disulfide conjugate

<400> SEQUENCE: 15
naaaaaaaaa aaaaaaaaaa attccttgcc t                                 31

<210> SEQ ID NO 16
<211> LENGTH: 75
<212> TYPE: DNA
<213> ORGANISM: Artificial Sequence
<220> FEATURE:
<223> OTHER INFORMATION: PCR amplimer

<400> SEQUENCE: 16
gaggctgacc tgaagcactt gaaggagaag gtgtctgcgg gagccgattt catcatcacg   60
cagcttttct ttgag                                                   75

<210> SEQ ID NO 17
<211> LENGTH: 119
<212> TYPE: DNA
<213> ORGANISM: Artificial Sequence
<220> FEATURE:
<223> OTHER INFORMATION: PCR amplimer

<400> SEQUENCE: 17
tattggcagg ttaccccaaa ggccaccccg aagcagggag ctttgaggct gacctgaagc   60
acttgaagga gaaggtgtct gcgggagccg atttcatcat cacgcagctt ttctttgag  119

<210> SEQ ID NO 18
<211> LENGTH: 294
<212> TYPE: DNA
<213> ORGANISM: Artificial Sequence
<220> FEATURE:
<223> OTHER INFORMATION: PCR amplimer

<400> SEQUENCE: 18
ccttgaacag gtggaggcca gcctctcctg actgtcatcc ctattggcag gttaccccaa   60
aggccacccc gaagcaggga ctttgaggc tgacctgaag cacttgaagg agaaggtgtc  120
tgcgggagcc gatttcatca tcacgcagct tttctttgag gctgacacat tcttccgctt  180
tgtgaaggca tgcaccgaca tgggcatcac ttgccccatc gtcccgggga tctttcccat  240
ccaggtgagg ggcccaggag agcccataag ctccctccac cccactctca ccgc        294
```

```
<210> SEQ ID NO 19
<211> LENGTH: 20
<212> TYPE: DNA
<213> ORGANISM: Artificial Sequence
<220> FEATURE:
<223> OTHER INFORMATION: polyethylenglycolamino-modified oligonucleotide
<220> FEATURE:
<221> NAME/KEY: misc_feature
<222> LOCATION: (20)..(20)
<223> OTHER INFORMATION: n is deoxythymidine 3' substituted with a
      polyoxyethylenamino group
<220> FEATURE:
<221> NAME/KEY: misc_feature
<222> LOCATION: (20)..(20)
<223> OTHER INFORMATION: n is deoxythymidine substituted in 3' with a
      polyethyleneglycolamino group

<400> SEQUENCE: 19
atcggctccc gcagacaccn                                              20

<210> SEQ ID NO 20
<211> LENGTH: 34
<212> TYPE: DNA
<213> ORGANISM: Artificial Sequence
<220> FEATURE:
<223> OTHER INFORMATION: oligonucleotide probe modified with gold
      nanoparticle
<220> FEATURE:
<221> NAME/KEY: misc_feature
<222> LOCATION: (1)..(1)
<223> OTHER INFORMATION: n is a deoxyadenosine residue modified in 5'
      with an epiandrosterone disulfide-gold
      nanoparticle-epiandrosterone disulfide conjugate

<400> SEQUENCE: 20
naaaaaaaaa aaaaaaaaaa gcgtgatgat gaaa                              34

<210> SEQ ID NO 21
<211> LENGTH: 33
<212> TYPE: DNA
<213> ORGANISM: Artificial Sequence
<220> FEATURE:
<223> OTHER INFORMATION: oligonucleotide probe modified with gold
      nanoparticle
<220> FEATURE:
<221> NAME/KEY: misc_feature
<222> LOCATION: (1)..(1)
<223> OTHER INFORMATION: n is a deoxyadenosine residue modified in 5'
      with an epiandrosterone disulfide-gold
      nanoparticle-epiandrosterone disulfide conjugate

<400> SEQUENCE: 21
naaaaaaaaa aaaaaaaaaa cctcaaagaa aag                               33

<210> SEQ ID NO 22
<211> LENGTH: 75
<212> TYPE: DNA
<213> ORGANISM: homo sapiens

<400> SEQUENCE: 22
gaggctgacc tgaagcactt gaaggagaag gtgtctgcgg gagccgattt catcatcacg  60 cagctttttct ttgag                                                  75

<210> SEQ ID NO 23
<211> LENGTH: 75
<212> TYPE: DNA
<213> ORGANISM: homo sapiens
```

```
<400> SEQUENCE: 23
gaggctgacc tgaagcactt gaaggagaag gtgtctgcgg gagtcgattt catcatcacg      60
cagcttttct ttgag                                                      75

<210> SEQ ID NO 24
<211> LENGTH: 21
<212> TYPE: DNA
<213> ORGANISM: Artificial Sequence
<220> FEATURE:
<223> OTHER INFORMATION: polyethylenglycolamino-modified oligonucleotide
<220> FEATURE:
<221> NAME/KEY: misc_feature
<222> LOCATION: (21)..(21)
<223> OTHER INFORMATION: n is deoxycytidine substituted in 3' with a
      tripolyethyleneglycol amino group

<400> SEQUENCE: 24
cccgcagaca ccttctcctt n                                               21

<210> SEQ ID NO 25
<211> LENGTH: 34
<212> TYPE: DNA
<213> ORGANISM: Artificial Sequence
<220> FEATURE:
<223> OTHER INFORMATION: oligonucleotide probe modified with gold
      nanoparticle
<220> FEATURE:
<221> NAME/KEY: misc_feature
<222> LOCATION: (1)..(1)
<223> OTHER INFORMATION: n is a deoxyadenosine residue modified in 5'
      with an epiandrosterone disulfide-gold
      nanoparticle-epiandrosterone disulfide conjugate

<400> SEQUENCE: 25
naaaaaaaaa aaaaaaaaaa tgatgaaatc gact                                 34

<210> SEQ ID NO 26
<211> LENGTH: 32
<212> TYPE: DNA
<213> ORGANISM: Artificial Sequence
<220> FEATURE:
<223> OTHER INFORMATION: oligonucleotide probe modified with gold
      nanoparticle
<220> FEATURE:
<221> NAME/KEY: misc_feature
<222> LOCATION: (1)..(1)
<223> OTHER INFORMATION: n is a deoxyadenosine residue modified in 5'
      with an epiandrosterone disulfide-gold
      nanoparticle-epiandrosterone disulfide conjugate

<400> SEQUENCE: 26
naaaaaaaaa aaaaaaaaaa atgaaatcgg ct                                   32

<210> SEQ ID NO 27
<211> LENGTH: 100
<212> TYPE: DNA
<213> ORGANISM: homo sapiens

<400> SEQUENCE: 27
aagcacttga aggagaaggt gtctgcggga gccgatttca tcatcacgca gcttttcttt     60
gaggctgaca cattcttccg ctttgtgaag gcatgcaccg                          100

<210> SEQ ID NO 28
<211> LENGTH: 19
<212> TYPE: DNA
<213> ORGANISM: Artificial Sequence
<220> FEATURE:
```

```
<223> OTHER INFORMATION: amino-modified oligonucleotide
<220> FEATURE:
<221> NAME/KEY: misc_feature
<222> LOCATION: (19)..(19)
<223> OTHER INFORMATION: n is deoxythymidine substituted in 3' with an
      amino group

<400> SEQUENCE: 28
tcggctcccg cagacaccn                                                    19

<210> SEQ ID NO 29
<211> LENGTH: 34
<212> TYPE: DNA
<213> ORGANISM: Artificial Sequence
<220> FEATURE:
<223> OTHER INFORMATION: oligonucleotide probe modified with gold
      nanoparticle
<220> FEATURE:
<221> NAME/KEY: misc_feature
<222> LOCATION: (1)..(1)
<223> OTHER INFORMATION: n is a deoxyadenosine residue modified in 5'
      with an epiandrosterone disulfide-gold
      nanoparticle-epiandrosterone disulfide conjugate

<400> SEQUENCE: 29
naaaaaaaaa aaaaaaaaaa cctcaaagaa aagc                                   34

<210> SEQ ID NO 30
<211> LENGTH: 39
<212> TYPE: DNA
<213> ORGANISM: Artificial Sequence
<220> FEATURE:
<223> OTHER INFORMATION: oligonucleotide probe modified with gold
      nanoparticle
<220> FEATURE:
<221> NAME/KEY: misc_feature
<222> LOCATION: (1)..(1)
<223> OTHER INFORMATION: n is a deoxyadenosine residue modified in 5'
      with an epiandrosterone disulfide-gold
      nanoparticle-epiandrosterone disulfide conjugate

<400> SEQUENCE: 30
naaaaaaaaa aaaaaaaaaa aaaagcggaa gaatgtgtc                              39

<210> SEQ ID NO 31
<211> LENGTH: 17
<212> TYPE: DNA
<213> ORGANISM: Artificial Sequence
<220> FEATURE:
<223> OTHER INFORMATION: amine-modified oligonucleotide
<220> FEATURE:
<221> NAME/KEY: misc_feature
<222> LOCATION: (17)..(17)
<223> OTHER INFORMATION: n is 3' amino-substituted deoxycytidine
      (4-Amino-1-(4-amino-5-hydroxymethyl-tetrahydro-furan-2-yl)-1H-
      pyrimidin-2-one)

<400> SEQUENCE: 31
tgatgaaatc ggctccn                                                      17

<210> SEQ ID NO 32
<211> LENGTH: 20
<212> TYPE: DNA
<213> ORGANISM: Artificial Sequence
<220> FEATURE:
<223> OTHER INFORMATION: "a20" oligonucleotide probe

<400> SEQUENCE: 32
aaaaaaaaaa aaaaaaaaaa                                                   20
```